US011439762B2

(12) United States Patent
Toporek et al.

(10) Patent No.: US 11,439,762 B2
(45) Date of Patent: Sep. 13, 2022

(54) DATA COLLECTION APPARATUS FOR ATTACHMENT TO AN INJECTION DEVICE

(71) Applicant: SANOFI-AVENTIS DEUTSCHLAND GMBH, Frankfurt am Main (DE)

(72) Inventors: Maurice Toporek, Frankfurt am Main (DE); Matthias Felber, Will (CH); Christoph Matthias Gugl, Will (CH); Marcus-Meinolf Dittrich, Frankfurt am Main (DE); Christian Nessel, Frankfurt am Main (DE); Stephan Riedel, Frankfurt am Main (DE); Armin Koller, Will (CH); Alexander Heinrich, Will (CH); Florian Eberli, Will (CH); Philipp Muller, Will (CH); Sven Zwicker, Will (CH)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 317 days.

(21) Appl. No.: 16/742,219

(22) Filed: Jan. 14, 2020

(65) Prior Publication Data

US 2020/0147315 A1    May 14, 2020

Related U.S. Application Data

(63) Continuation of application No. 15/579,656, filed as application No. PCT/EP2016/063139 on Jun. 9, 2016, now Pat. No. 10,874,802.

(30) Foreign Application Priority Data

Jun. 9, 2015 (EP) .................................... 15171252
Dec. 10, 2015 (EP) .................................... 15199308

(51) Int. Cl.
*A61M 5/31* (2006.01)
*A61M 5/315* (2006.01)

(52) U.S. Cl.
CPC .... *A61M 5/31551* (2013.01); *A61M 5/31528* (2013.01); *A61M 5/31585* (2013.01);
(Continued)

(58) Field of Classification Search
CPC .......... A61M 5/31551; A61M 5/31528; A61M 5/31585; A61M 2005/3125;
(Continued)

(56) References Cited

U.S. PATENT DOCUMENTS

| 533,575 A | 2/1895 | Wilkens |
| 5,226,895 A | 7/1993 | Harris |
| (Continued) | | |

FOREIGN PATENT DOCUMENTS

| CN | 101727540 | 6/2010 |
| CN | 102413855 | 4/2012 |
| (Continued) | | |

OTHER PUBLICATIONS

European Search Report for EP Application No. 12710104.6, dated Sep. 21, 2017.

(Continued)

*Primary Examiner* — Amber R Stiles
(74) *Attorney, Agent, or Firm* — Fish & Richardson P.C.

(57) ABSTRACT

A data collection device comprises: a first portion having one or more features configured for attaching of the first portion to a dosage knob of an injection device; a second portion rotatably coupled with the first portion, wherein at least part of the second portion is movable axially relative to the first portion; a sensor arrangement configured to detect rotation of the first portion relative to the second portion; and a processor arrangement configured to, based on said detected movement, determine a medicament amount expelled by the injection device, wherein the coupling arrangement is configured to provide a non-permanent coupling between the first portion and the dosage knob of the injection device.

20 Claims, 19 Drawing Sheets

(52) U.S. Cl.
CPC ............... *A61M 2005/3125* (2013.01); *A61M 2205/3306* (2013.01); *A61M 2205/502* (2013.01); *A61M 2205/52* (2013.01); *A61M 2205/581* (2013.01)

(58) Field of Classification Search
CPC .... A61M 2205/3306; A61M 2205/502; A61M 2205/52; A61M 2205/581
See application file for complete search history.

(56) References Cited

U.S. PATENT DOCUMENTS

| | | | |
|---|---|---|---|
| 5,279,586 A | 1/1994 | Balkwill |
| 5,304,152 A | 4/1994 | Sams |
| 5,320,609 A | 6/1994 | Haber et al. |
| 5,331,953 A | 7/1994 | Andersson et al. |
| 5,383,865 A | 1/1995 | Michel |
| 5,480,387 A | 1/1996 | Gabriel et al. |
| 5,505,704 A | 4/1996 | Pawelka et al. |
| 5,509,905 A | 4/1996 | Michel |
| 5,582,598 A | 12/1996 | Chanoch |
| 5,626,566 A | 5/1997 | Petersen et al. |
| 5,662,612 A | 9/1997 | Niehoff |
| 5,674,204 A | 10/1997 | Chanoch |
| 5,688,251 A | 11/1997 | Chanoch |
| 5,921,966 A | 7/1999 | Bendek et al. |
| 5,961,495 A | 10/1999 | Walters et al. |
| 6,004,297 A | 12/1999 | Steenfeldt-Jensen et al. |
| 6,193,698 B1 | 2/2001 | Kirchhofer et al. |
| 6,221,046 B1 | 4/2001 | Burroughs et al. |
| 6,235,004 B1 | 5/2001 | Steenfeldt-Jensen et al. |
| 6,246,322 B1 | 6/2001 | LeDain et al. |
| 6,248,095 B1 | 6/2001 | Giambattista et al. |
| 6,277,099 B1 | 8/2001 | Strowe et al. |
| 6,482,185 B1 | 11/2002 | Hartmann |
| 6,500,169 B1 | 12/2002 | Deng |
| 6,585,698 B1 | 7/2003 | Packman et al. |
| 6,620,133 B1 | 9/2003 | Steck |
| 6,869,413 B2 | 3/2005 | Langley et al. |
| 6,899,698 B2 | 5/2005 | Sams |
| 6,936,032 B1 | 8/2005 | Bush, Jr. et al. |
| 7,008,399 B2 | 3/2006 | Larsen et al. |
| 7,241,278 B2 | 7/2007 | Moller |
| 7,749,186 B2 | 7/2010 | Kohlbrenner et al. |
| 8,052,655 B2 | 11/2011 | Moller et al. |
| 8,197,449 B2 | 6/2012 | Nielsen et al. |
| 8,231,573 B2 | 7/2012 | Edwards et al. |
| 8,556,847 B2 | 10/2013 | Kohlbrenner et al. |
| 8,556,865 B2 | 10/2013 | Krulevitch et al. |
| 8,556,866 B2 | 10/2013 | Krulevitch et al. |
| 8,556,867 B2 | 10/2013 | Krulevitch et al. |
| 8,560,271 B2 | 10/2013 | Koehler et al. |
| 8,613,719 B2 | 12/2013 | Karratt et al. |
| 8,672,899 B2 | 3/2014 | Diller et al. |
| 8,771,238 B2 | 7/2014 | Nielsen et al. |
| 8,994,382 B2 | 3/2015 | Nielsen et al. |
| 9,289,559 B2 | 3/2016 | Pedersen et al. |
| 9,522,238 B2 | 12/2016 | Nielsen et al. |
| 9,526,842 B2 | 12/2016 | Oh et al. |
| 9,623,188 B2 | 4/2017 | Nielsen et al. |
| 9,649,448 B2 | 5/2017 | Madsen |
| 9,672,328 B2 | 6/2017 | Saint et al. |
| 9,734,302 B2 | 8/2017 | Nielsen et al. |
| 9,959,391 B2 | 5/2018 | Saint et al. |
| 10,105,489 B2 | 10/2018 | Edwards et al. |
| 10,213,554 B2 | 2/2019 | Andersen et al. |
| 10,383,996 B2 | 8/2019 | Miller et al. |
| 10,420,895 B2 | 9/2019 | Erbstein et al. |
| 10,446,269 B2 | 10/2019 | Groeschke et al. |
| 10,471,213 B2 | 11/2019 | Schabbach et al. |
| 10,483,000 B2 | 11/2019 | Saint et al. |
| 10,593,232 B2 | 3/2020 | Bauss |
| 10,617,827 B2 | 4/2020 | Hautaviita et al. |
| 10,695,504 B2 | 6/2020 | Nielsen et al. |
| 10,857,304 B2 | 12/2020 | Byerly |
| 11,020,533 B2 | 6/2021 | Erbstein et al. |
| 11,278,677 B2 | 3/2022 | Erbstein et al. |
| 2002/0052578 A1 | 5/2002 | Moller |
| 2002/0120235 A1 | 8/2002 | Enggaard |
| 2002/0143288 A1 | 10/2002 | Larsen et al. |
| 2002/0163435 A1 | 11/2002 | Kosaka |
| 2002/0188419 A1 | 12/2002 | Slate et al. |
| 2003/0036762 A1 | 2/2003 | Kerr et al. |
| 2003/0050609 A1 | 3/2003 | Sams |
| 2004/0059299 A1 | 3/2004 | Moller |
| 2004/0085215 A1 | 5/2004 | Moberg et al. |
| 2004/0140972 A1 | 7/2004 | Hirota et al. |
| 2004/0210199 A1 | 10/2004 | Atterbury et al. |
| 2004/0267207 A1 | 12/2004 | Veasey et al. |
| 2005/0113765 A1 | 5/2005 | Veasey et al. |
| 2005/0283065 A1 | 12/2005 | Babayoff |
| 2006/0135907 A1 | 6/2006 | Remde et al. |
| 2006/0153693 A1 | 7/2006 | Fiechter et al. |
| 2007/0123829 A1 | 5/2007 | Atterbury et al. |
| 2007/0210828 A1 | 9/2007 | Won et al. |
| 2008/0033369 A1 | 2/2008 | Kohlbrenner et al. |
| 2009/0043253 A1 | 2/2009 | Podaima |
| 2009/0069742 A1 | 3/2009 | Larsen |
| 2009/0194104 A1 | 8/2009 | Van Sickle |
| 2009/0275916 A1 | 11/2009 | Harms et al. |
| 2010/0324496 A1 | 12/2010 | Plumptre et al. |
| 2011/0112474 A1 | 5/2011 | Bochenko et al. |
| 2011/0238017 A1 | 9/2011 | Watanabe et al. |
| 2011/0270214 A1 | 11/2011 | Jorgensen et al. |
| 2011/0313349 A1* | 12/2011 | Krulevitch ............... A61M 5/24 604/65 |
| 2012/0092670 A1 | 4/2012 | Chatow et al. |
| 2013/0197445 A1 | 8/2013 | Schabbach et al. |
| 2013/0204227 A1 | 8/2013 | Bochenko et al. |
| 2013/0274680 A1 | 10/2013 | Veasey et al. |
| 2013/0310756 A1* | 11/2013 | Whalley ............... A61M 5/3129 604/189 |
| 2014/0005950 A1 | 1/2014 | Groeschke et al. |
| 2014/0194826 A1 | 7/2014 | Nielsen et al. |
| 2014/0194829 A1 | 7/2014 | Baek et al. |
| 2015/0202375 A1 | 7/2015 | Schabbach et al. |
| 2016/0235925 A1 | 8/2016 | Kuhn et al. |
| 2017/0182258 A1 | 6/2017 | Michael |
| 2017/0189625 A1 | 7/2017 | Cirillo et al. |
| 2017/0368263 A1 | 12/2017 | Ploch |
| 2018/0001027 A1 | 1/2018 | Klemm et al. |
| 2018/0154086 A1 | 6/2018 | Toporek et al. |
| 2019/0381248 A1 | 12/2019 | Erbstein et al. |
| 2020/0013503 A1 | 1/2020 | Groeschke et al. |
| 2020/0197614 A1 | 6/2020 | Erbstein et al. |
| 2022/0001111 A1* | 1/2022 | Toporek ............ A61M 5/31585 |
| 2022/0134009 A1 | 5/2022 | Erbstein et al. |

FOREIGN PATENT DOCUMENTS

| | | |
|---|---|---|
| CN | 102458514 | 5/2012 |
| CN | 103561801 | 2/2014 |
| CN | 104203315 | 12/2014 |
| CN | 104245020 | 12/2014 |
| CN | 104411349 | 3/2015 |
| CN | 103648555 | 3/2019 |
| DE | 29904864 | 8/2000 |
| DE | 102004063664 | 7/2006 |
| EP | 0777123 | 6/1997 |
| EP | 0937471 | 8/1999 |
| EP | 0937476 | 8/1999 |
| EP | 2060284 | 5/2009 |
| EP | 2182456 | 5/2010 |
| EP | 2692378 | 2/2014 |
| EP | 2762184 | 8/2014 |
| EP | 2401012 | 4/2020 |
| JP | H11-267207 | 10/1999 |
| JP | 2000-506030 | 5/2000 |
| JP | 2001-087386 | 4/2001 |
| JP | 2001-509426 | 7/2001 |
| JP | 2004-523282 | 8/2004 |
| JP | 2008-516711 | 5/2008 |
| JP | 2009-530002 | 8/2009 |
| JP | 2010-534085 | 11/2010 |

(56) References Cited

FOREIGN PATENT DOCUMENTS

| | | |
|---|---|---|
| JP | 2012-500695 | 1/2012 |
| JP | 2012-504440 | 2/2012 |
| JP | 2012-135594 | 7/2012 |
| JP | 2012-519025 | 8/2012 |
| JP | 2012-519028 | 8/2012 |
| JP | 2014-516599 | 7/2014 |
| JP | 2014-520584 | 8/2014 |
| WO | WO 1990/009202 | 8/1990 |
| WO | WO 1993/016743 | 9/1993 |
| WO | WO 1997/030742 | 8/1997 |
| WO | WO 1999/002210 | 1/1999 |
| WO | WO 1999/038554 | 8/1999 |
| WO | WO 2001/010484 | 2/2001 |
| WO | WO 2002/058767 | 8/2002 |
| WO | WO 2006/045525 | 5/2006 |
| WO | WO 2007/107564 | 9/2007 |
| WO | WO 2009/013736 | 1/2009 |
| WO | WO 2009/083600 | 7/2009 |
| WO | WO 2010/023303 | 3/2010 |
| WO | WO 2010/037828 | 4/2010 |
| WO | WO 2010/052275 | 5/2010 |
| WO | WO 2010/098927 | 9/2010 |
| WO | WO 2010/098928 | 9/2010 |
| WO | WO 2010/098931 | 9/2010 |
| WO | WO 2010/142598 | 12/2010 |
| WO | WO 2012/046199 | 4/2012 |
| WO | WO 2012/127046 | 9/2012 |
| WO | WO 2012/130703 | 10/2012 |
| WO | WO 2013/004844 | 1/2013 |
| WO | WO 2013/120774 | 8/2013 |
| WO | WO 2013/120778 | 8/2013 |
| WO | WO 2013/177135 | 11/2013 |
| WO | WO 2014/023763 | 2/2014 |
| WO | WO 2014/037331 | 3/2014 |
| WO | WO 2014/064691 | 5/2014 |
| WO | WO 2014/111337 | 7/2014 |
| WO | WO 2014/128156 | 8/2014 |
| WO | WO 2014/173768 | 10/2014 |
| WO | WO 2014/173774 | 10/2014 |
| WO | WO 2014/180744 | 11/2014 |
| WO | WO 2016/131713 | 8/2016 |
| WO | WO 2019/173097 | 9/2019 |

OTHER PUBLICATIONS

PCT International Preliminary Report on Patentability in Application No. PCT/EP2012/055252, dated Sep. 24, 2013, 9 pages.
PCT International Search Report for International Application No. PCT/EP2012/055252, completed Oct. 31, 2012.
[No Author Listed] [online], ""NovoPen 5—Novo Nordisk,"" Youtube, Jul. 5, 2012, retrieved on Sep. 10, 2021, <https://www.youtube.com/watch?v=u3EX_0KzkQE>, 1 page [Video Submission].
[No Author Listed], "HumaPen Ergo Manual", Eli Lilly and Company Ltd., 2003, 2 pages.
[No Author Listed], "Technical Dossier for the HumaPen Pen-Injector Family," Eli Lilly & Company—Pharmaceutical Delivery Systems, Aug. 15, 2000, 17 pages.
EP Notice of Opposition by Di-Care Zrt. in Patent Application No. 16704003.9, dated Aug. 27, 2021, 33 pages.
EP Notice of Opposition by Herzog IP Patentanwaits GmbH in Patent Application No. 12710104.6, dated Aug. 31, 2021, 50 pages.
EP Notice of Opposition by Herzog IP Patentanwaits GMbH in Patent Application No. 16704003.9, dated Aug. 31, 2021, 126 pages.

*Novo Nordisk A/S*, Plaintiff, v. *Sanofi-Aventis U.S. LLC and Sanofi-Aventis*, Defendants, Case No. 3:07-cv-03206-MLC-JJH, Affidavit of Charles E. Clemens, filed Sep. 10, 2007, 82 pages.
Rustige, "Important New Safety Reminder Regarding the HumaPen Ergo", HumaPen Ergo Customer letter from Eli Lilly Canada, Dec. 11, 2001, 2 pages.
European Search Report in Application No. 15155758.4, dated Sep. 4, 2015, 3 pages.
International Preliminary Report on Patentability in Application No. PCT/EP2016/052987, dated Aug. 22, 2017, 7 pages.
International Search Report and Written Opinion in International Application No. PCT/EP2016/052987, dated Apr. 21, 2016, 10 pages.
Extended European Search Report in Patent Application No. 15171252.8, dated Dec. 9, 2015, 7 pages.
International Search Report and Written Opinion in International Application No. PCT/EP2016/063139, dated Sep. 22, 2016, 12 pages.
International Preliminary Report on Patentability in International Application No. PCT/EP2016/063139, dated Dec. 12, 2017, 7 pages.
Injecting Insulin With the Lantus SoloSTAR Pen video, available online as of Oct. 29, 2012 at https://www.youtube.com/watch?v=g7JLG36ZO-U (Year: 2012).
EP Notice of Opposition by Di-Care Zrt. in Patent Application No. 16729241.6, dated Feb. 8, 2021, 17 pages.
[No Author Listed] [online], "Diabetes Education: How to Inject Insulin," available online as of Nov. 14, 2014, URL:<https://www.youtube.com/watch?v=ycp7BbFhG44>, 1 page [Video Submission].
[No Author Listed] [online], "How to use SoloStar Pen for Injecting Lantus (Glargine) and Apidra (Glulisine) Insulin Music Version," available online as of May 17, 2013, URL:<https://www.youtube.com/watch?v=ZcfKG0Mp3kI>, 1 page [Video Submission].
[No Author Listed], "Comparison of publication EP201012B1 with publication WO2010/098928," cited in European Opposition in EP Application No. 16729241.6, unknown date, 26 pages.
Brief Communication in European Application No. 12710104.6, dated Jan. 20, 2022, 70 pages.
Brief Communication in European Application No. 16704003.9, dated Jan. 21, 2022, 81 pages.
Brief Communication in European Application No. 16729241.6, dated Apr. 11, 2022, 28 pages.
Brief Communication in European Application No. 16729241.6, dated Apr. 7, 2022, 11 pages.
Brief Communication in European Application No. 16729241.6, dated Apr. 7, 2022, 22 pages.
Written Submission in European Opposition in European Application No. 16729241.6, dated Apr. 4, 2022, 30 pages.
Brief Communication in European Application No. 12710104.6, dated May 6, 2022, 37 pages.
Brief Communication in European Application No. 16704003.9, dated May 5, 2022, 152 pages.
Dictionary.cambridge.org [online], "Button," 2014, retrieved on Jan. 3, 2022, retrieved from URL <https://dictionary.cambridge.org/de/worterbuch/englisch/button>, 11 pages.
EP Notice of Opposition by Ferring International Center S.A. in Patent Application No. 9737825.1, dated Jun. 18, 2013, 22 pages.
EP Response to Communication in Opposition by Herzog IP Patentanwalts GMbH in Patent Application No. 16704003.9, dated Jun. 19, 2019, 7 pages.

* cited by examiner

DATA COLLECTION APPARATUS FOR ATTACHMENT TO AN INJECTION DEVICE

CROSS REFERENCE TO RELATED APPLICATIONS

The present application is a continuation of U.S. application Ser. No. 15/579,656, filed Dec. 5, 2017, which is the U.S. national stage entry under 35 USC § 371 of International Patent Application No. PCT/EP2016/063139, filed on Jun. 9, 2016, which claims priority to European Patent Application No. 15171252.8, filed on Jun. 9, 2015, and European Patent Application No. 15199308.6, filed on Dec. 10, 2015, the entire contents of all of which are incorporated herein by reference.

TECHNICAL FIELD

The present disclosure generally relates to a data collection device for attachment to an injection device and collecting medicament dosage information therefrom.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dose window or display of the insulin pen. The dose is then injected by inserting the needle into a suited skin portion and pressing an injection button of the insulin pen. To be able to monitor insulin injection, for instance to prevent false handling of the insulin pen or to keep track of the doses already applied, it is desirable to measure information related to a condition and/or use of the injection device, such as for instance information on the injected insulin dose.

SUMMARY

An aspect of the disclosure provides a data collection device comprising a first portion configured for attachment to an injection device, a second portion rotatably attached to the first portion, a sensor arrangement configured to detect rotation of the first portion relative to the second portion and a processor arrangement configured to, based on said detected movement, determine a medicament amount expelled by the injection device.

Since the data collection device does not utilize recognition of characters on the injection device to determine a medicament dosage amount, the data collection device may, optionally, be configured so that it does not obscure display of a currently programmed dosage, avoiding the need to provide an additional display of the dosage amount for viewing by the user. In addition, the determination of the medicament dosage amount may be less computationally intensive than optical character recognition techniques.

Additionally, the data collection device may be implemented in an embodiment wherein the second portion comprises an outer portion having first electrical contacts, the second portion comprises an inner portion having second electrical contacts and the inner portion is axially movable relative to the outer portion to engage said first electrical contacts with said second electrical contacts when pressure is applied to the outer portion. For instance, engagement of the first and second electrical contacts may activate the data collection device.

Further additionally data collection device may comprise a piezo-electric generator arranged to power the data collection device when pressure is applied to the outer portion.

Additionally and/or alternatively, the data collection device may comprise a timer triggered when said first electrical contacts are engaged and/or disengaged from the second electrical contacts.

Additionally and/or alternatively, the data collection device may be configured to determine an elapsed time since the timer was last triggered and to generate an alert if the elapsed time is inconsistent with a threshold condition.

Additionally and/or alternatively, the data collection device may have the processor arrangement configured to determine a time stamp for the administration of the medicament dosage using said timer and to store the determined medicament dosage and said time stamp.

Additionally and/or alternatively, the data collection device may have the processor arrangement configured to transmit a log of determined medicament dosages and time stamp information to another device.

Additionally and/or alternatively, the data collection device may be configured to switch between a first configuration in which rotation of the first portion relative to the second portion is prevented and a second configuration in which the first portion can be rotated relative to the second portion. For example, the second portion may be axially movable relative to the first portion to switch between said first configuration and said second configuration.

Additionally and/or alternatively, the data collection device may have the sensor arrangement comprising one or more of an optical sensor, a magnetic sensor, a capacitive sensor or a mechanical sensor.

Additionally and/or alternatively, the data collection device may have the first portion being configured to be attached to a rotatable component of the injection device.

Additionally and/or alternatively, the data collection device may comprise a transfer arrangement arranged to engage a rotatable component of the injection device wherein the first portion is configured to be attached to a rotatable component of the injection device and wherein the transfer arrangement is configured to rotate the first portion relative to the second portion when said rotatable component rotates.

Additionally and/or alternatively, the data collection device may have the transfer arrangement comprising a friction wheel.

An aspect of the disclosure provides a medicament administration apparatus which comprises an injection device having a rotatable component configured to rotate as a medicament is expelled from the injection device and a data collection device as set out in the preceding sections.

Additionally and/or alternatively, the medicament administration apparatus may have the injection device comprising an injection button arranged to cause expulsion of the medicament from the injection device and may have the second portion being arranged to press on the injection button when pressure is applied to the second portion.

Additionally and/or alternatively, the medicament administration apparatus may comprise an injection device comprising a rotatable component configured to rotate as a medicament is expelled from the injection device; and a data collection device as set out above wherein the transfer arrangement is arranged to engage a rotatable sleeve of the injection device.

In some embodiments, the injection device is a disposable injection device and the data collection device is configured to be releasably attachable to the injection device. In some embodiments, the injection device may be a reusable injection device and the data collection device may be configured to be permanently attached to the injection device. Further, the injection device may be an injector pen.

An aspect of the disclosure provides a data collection device comprising a first portion having one or more features configured for attaching of the first portion to a dosage knob of an injection device, a second portion rotatably coupled with the first portion, wherein at least part of the second portion is movable axially relative to the first portion, a sensor arrangement configured to detect rotation of the first portion relative to the second portion, and a processor arrangement configured to, based on said detected movement, determine a medicament amount expelled by the injection device, wherein the coupling arrangement is configured to provide a non-permanent coupling between the first portion and the dosage knob of the injection device.

The first portion may have an internal surface formed of a deformable material.

The first portion may have an internal surface shaped to correspond to external features of the dosage knob of the injection device.

The first portion may have an internal surface configured to mate with external features of the dosage knob of the injection device.

The internal surface of the first portion may include grooves that correspond in shape with formations on the surface of the dosage knob of the injection device. The grooves may have mouths at an open end of the first portion and the grooves may taper to a narrower width away from the open end of the first portion.

The first portion may be provided with one or more external grip features to facilitate gripping of the first portion by a user to effect rotation of the data collection device relative to a housing of the injection device.

The user-accessible surface of the second portion may be larger than the user-accessible portion of the first portion when the data collection device is installed on the injection device.

The user-accessible surface of the first portion may be larger than the user-accessible portion of the second portion when the data collection device is installed on the injection device.

The second portion may be rotatably coupled with the first portion at a location that is closer radially to a longitudinal axis of the data collection device than it is to an outer diameter of the data collection device.

In some examples, the second portion may be rotatably coupled with the first portion at a location that is radially further from the longitudinal axis of the data collection device than it is to the outer diameter of the data collection device, and optionally wherein the location is axially coincident with the location of the dosage knob when the data collection device is installed on the injection device.

The first portion may include an element configured to fit closely around a dose button of the injection device when the data collection device is coupled to the injection device.

The data collection device may be configured to switch between a first configuration in which rotation of the first portion relative to the second portion is prevented and a second configuration in which the first portion can be rotated relative to the second portion.

The sensor arrangement may comprise one or more of an optical sensor, a magnetic sensor, a capacitive sensor or a mechanical sensor.

The data collection device may further comprise an electrical switch configured to be operated upon movement of at least part of the second portion relative to the first portion, wherein a force required to operate the electrical switch is lower than a force required to cause medicament delivery from the injection device.

An aspect of the disclosure provides a medicament administration apparatus which comprises an injection device comprising a rotatable component configured to rotate as a medicament is expelled from the injection device and a data collection device as set out above.

The injection device may comprise an injection button arranged to cause expulsion of the medicament from the injection device; and the second portion of the data collection device may be arranged to press on the injection button when pressure is applied to the second portion.

In some embodiments, the injection device is a disposable injection device and the data collection device is configured to be releasably attachable to the injection device. In some embodiments, the injection device may be a reusable injection device and the data collection device may be configured to be permanently attached to the injection device. Further, the injection device may be an injector pen.

BRIEF DESCRIPTION OF THE DRAWINGS

Non-limiting, exemplary embodiments of the disclosure will now be described with reference to the accompanying drawings, of which.

DETAILED DESCRIPTION

The present specification discloses a data collection device which is attachable to a proximal end of an injection device, such as a pen injector, such as to fit the injector device like a cap.

The data collection device is configured such that it can be push-fitted over a dosage knob or dose dialing knob of the injection device. In particular, a first portion of the data collection device includes a cavity that receives the dosage knob, and includes a deformable inner surface such as to provide a tight fit over the dosage knob and/or has features that mate closely with external features of the dosage knob. Through the push-fit features, the data collection device can easily be installed on the injection device, and can easily be removed through application of a removal force between the data collection device and the injection device in an axial direction. When installed, the data collection device is manipulated by the user in order to effect operation of the injection device. The data collection device when installed monitors quantities and times of medicament delivery from the injection pen. Medicament quantities can be transmitted, e.g. to a smartphone, and/or displayed on a display of the data collection device. By providing the data collection device with push-fit features, it can be located onto and used with a series of different injection devices and thus monitor a user's medicament treatment over multiple devices. Moreover, this can be achieved without impeding normal use of the injection device and without obscuring a dosage window of the injection device.

In the following, embodiments of the present disclosure will be described with reference to an insulin injection device. The present disclosure is however not limited to such applications and may equally well be deployed with injection devices that eject other medicaments.

Figure 1:
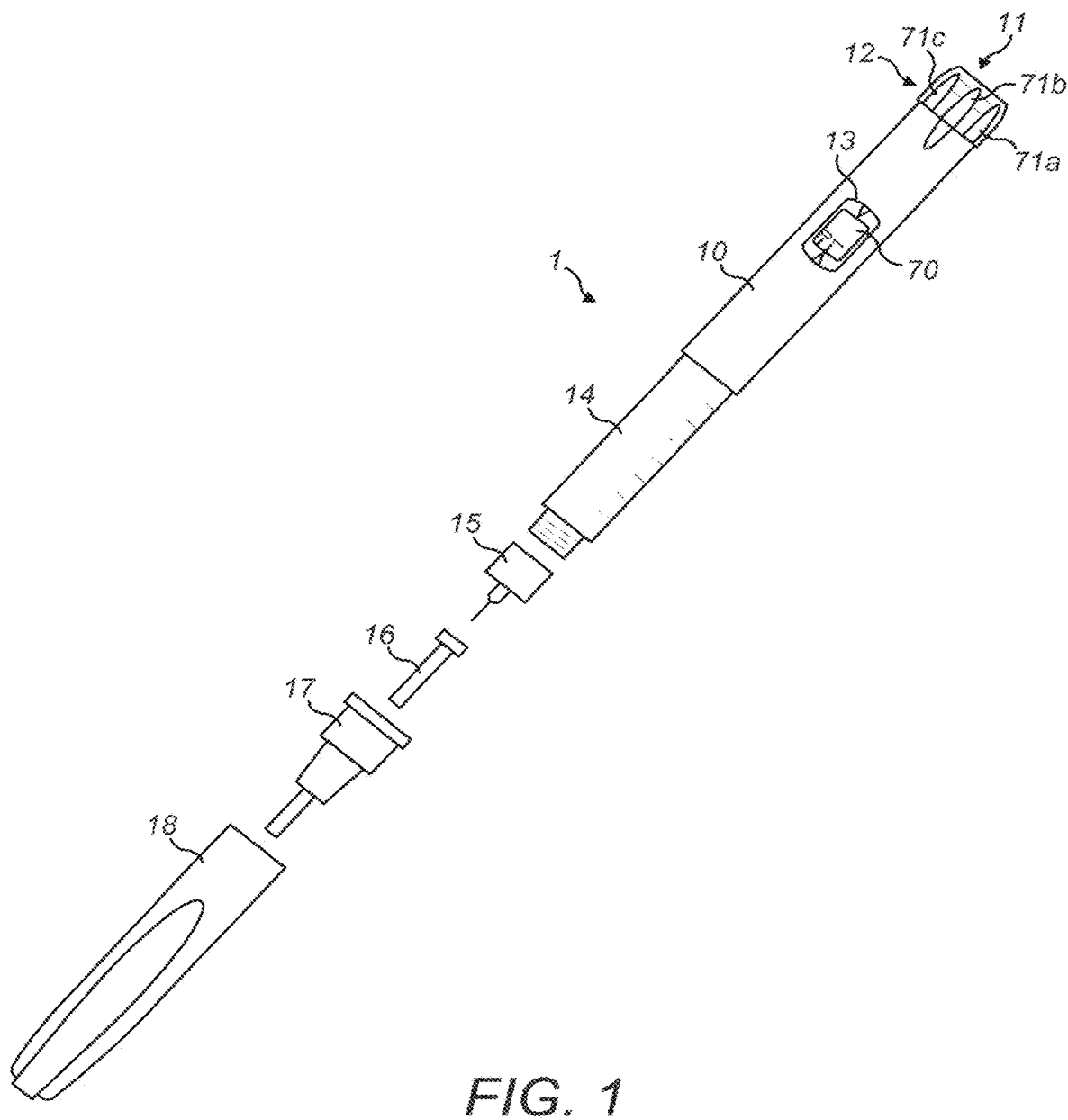
FIG. 1 shows an exploded view of an example injection device for use with a data collection device according to an embodiment of the disclosure.

FIG. 1 is an exploded view of a medicament delivery device. In this example, the medicament delivery device is an injection device 1, such as Sanofi's SoloSTAR® insulin injection pen.

The injection device 1 of FIG. 1 is a pre-filled, disposable injection pen that comprises a housing 10 and contains an insulin container 14, to which a needle 15 can be affixed. The needle is protected by an inner needle cap 16 and either an outer needle cap 17 or an alternative cap 18. An insulin dose to be ejected from injection device 1 can be programmed, or "dialed in" by turning a dosage knob 12, and a currently programmed dose is then displayed via dosage window 13, for instance in multiples of units. For example, where the injection device 1 is configured to administer human insulin, the dosage may be displayed in International Units (IU), wherein one IU is the biological equivalent of about 45.5 micrograms of pure crystalline insulin (1/22 mg). Other units may be employed in injection devices for delivering analogue insulin or other medicaments. It should be noted that the selected dose may equally well be displayed differently than as shown in the dosage window 13 in FIG. 1.

The dosage window 13 may be in the form of an aperture in the housing 10, which permits a user to view a limited portion of a number sleeve 70 that is configured to move when the dosage knob 12 is turned, to provide a visual indication of a currently programmed dose. The dosage knob 12 is rotated on a helical path with respect to the housing 10 when turned during programming.

In this example, the dosage knob 12 includes one or more formations 71a, 71b, 71c to facilitate attachment of a data collection device to be described hereinbelow.

The injection device 1 may be configured so that turning the dosage knob 12 causes a mechanical click sound to provide acoustical feedback to a user. The number sleeve 70 mechanically interacts with a piston in insulin container 14. When needle 15 is stuck into a skin portion of a patient, and then injection button 11 is pushed, the insulin dose displayed in display window 13 will be ejected from injection device 1. When the needle 15 of injection device 1 remains for a certain time in the skin portion after the injection button 11 is pushed, a high percentage of the dose is actually injected into the patient's body. Ejection of the insulin dose may also cause a mechanical click sound, which may be different from the sounds produced when using dosage knob 12.

In this embodiment, during delivery of the insulin dose, the dosage knob 12 is turned to its initial position in an axial movement (e.g., without rotation), while the number sleeve 70 is rotated to return to its initial position, e.g. to display a dose of zero units.

Injection device 1 may be used for several injection processes until either the insulin container 14 is empty or the expiration date of the medicament in the injection device 1 (e.g. 28 days after the first use) is reached.

Furthermore, before using injection device 1 for the first time, it may be necessary to perform a "prime shot" to remove air from insulin container 14 and needle 15, for instance by selecting two units of insulin and pressing injection button 11 while holding injection device 1 with the needle 15 upwards. For simplicity of presentation, in the following, it will be assumed that the ejected amounts substantially correspond to the injected doses, so that, for instance the amount of medicament ejected from the injection device 1 is equal to the dose received by the user. Nevertheless, differences (e.g. losses) between the ejected amounts and the injected doses may occur and may be taken into account.

Figure 2:
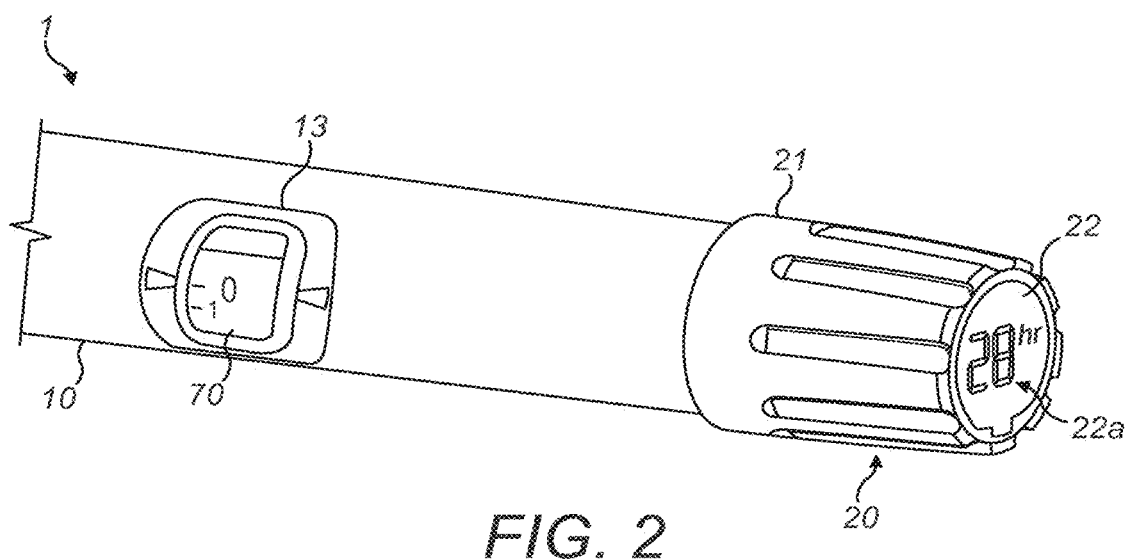
FIG. 2 depicts an example of a data collection device attached to the injection device of FIG. 1 according to an exemplary embodiment.

FIG. 2 is a perspective view of one end of the injection device 1 when a data collection device 20 according to an example embodiment is attached. The data collection device 20 includes a housing 21 and an end plate 22 with an optional display 22a. The data collection device 20 may take one of a number of different forms, as described below and as shown in the drawings.

Figure 3:
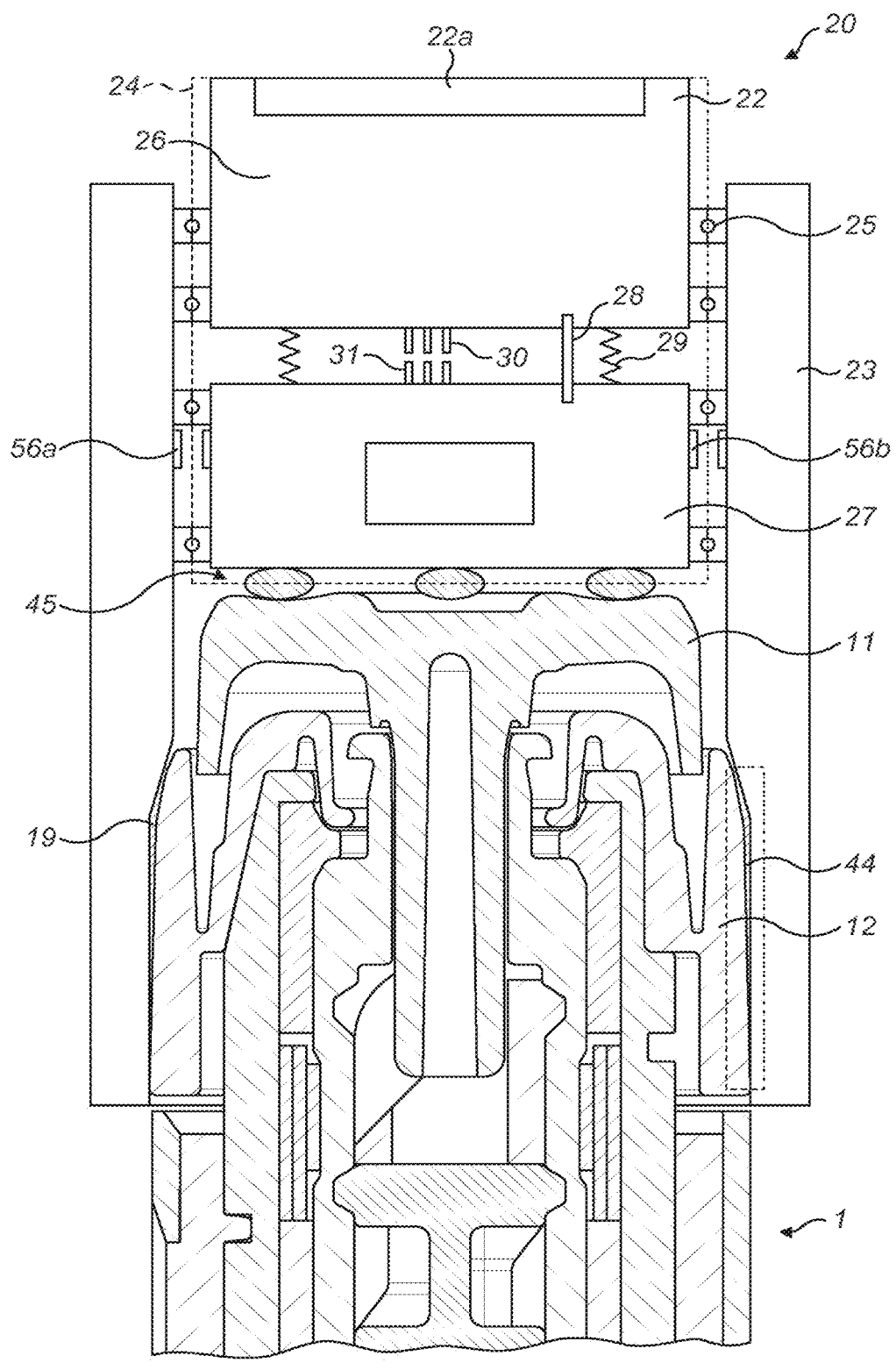
FIG. 3 is a cross-sectional view of the data collection device shown in FIG. 2 when attached to the injection device of FIG. 1.

FIG. 3 is a cross-sectional view of the data collection device 20 according to an embodiment, when attached to the injection device 1. The data collection device 20 includes a first portion 23 and a second portion 24, where the first portion 23 is capable of rotational movement relative to the second portion 24.

In this particular example, the first portion 23 is a sleeve that is positioned over the dosage knob 12. The first portion may have formations 19a, 19b, 19c that co-operate with the formations 71a, 71b, 71c on the dosage knob 12. Whether or not the formations 19a-c are provided on the first portion 23, the arrangement is such that, when the first portion 23 is rotated by a user during programming of the dosage, the dosage knob 12 also rotates and such that, when the dosage knob 12 rotates during expulsion of medicament, the first portion 23 also rotates.

Resilient padding, such as a foam rubber pad 44, may be provided within the formations 19a-c on the first portion 23, to allow for tolerances in the dimensions of the formations 19a-c on the first portion 23 and the formations 71a, 71b, 71c on the dosage knob 12 and/or to provide an engagement between the first portion 23 and the dosage knob 12 so that rotation of the first portion 23 causes rotation of the dosage knob 12 and vice versa. The resilient padding 44 may alternatively be made of another rubber or synthetic rubber material. The resilient padding 44 may be provided around the entire circumference of the first portion 23, or it may be provided at intermittent locations.

Figure 4A:
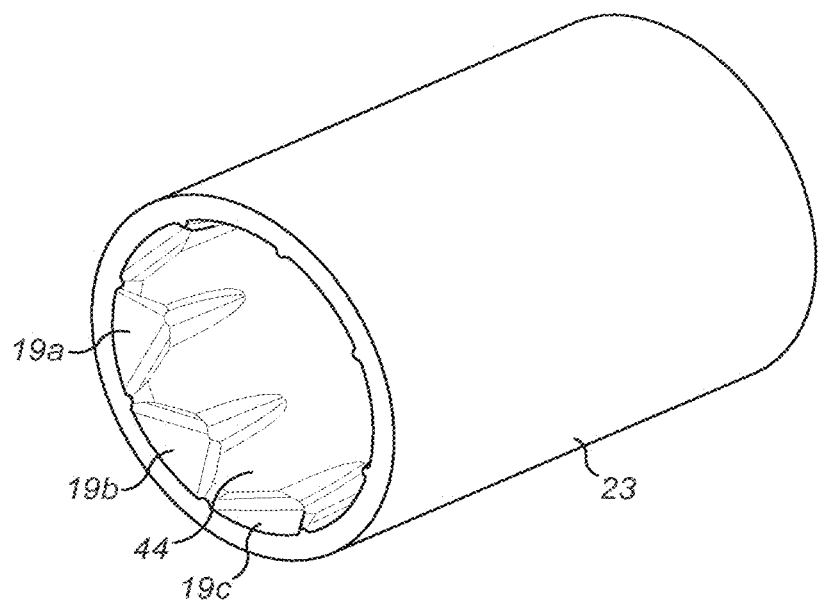
FIGS. 4*a*-4*d* are schematic drawings of example variations of a part of the data collection device of FIG. 2 that engages with the injection device.
Figure 4B:
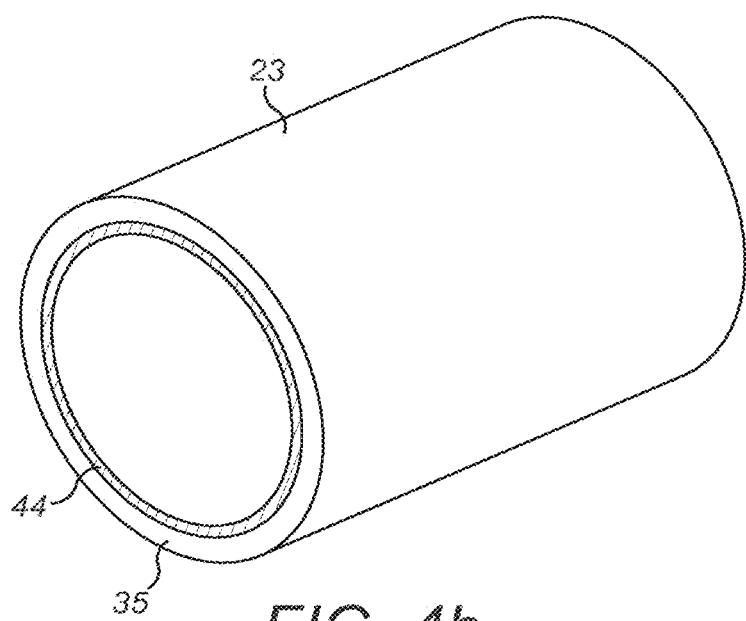

As shown in FIG. 4b, the resilient padding 44 may be provided alternatively to formations 19a-c on the first portion 23. In some embodiments, the inner surface of the first portion 23 at the distal end 35 (e.g., lowermost in FIG. 3) is substantially featureless. The inner surface may be generally cylindrical in shape. It may alternatively be generally conical, being wider at the distal end. It may alternatively be generally dome-shaped, being wider at the distal end.

Further, alternatively, the first portion 23 comprises a resilient padding of sufficient thickness to render formations that co-operate with the formations 71a, 71b, and 71c on the dosage knob. The padding is soft enough to conform to the surface of the dosage knob 12. For example, the padding is soft enough to conform to the formations on the surface of the dosage knob 12.

In some embodiments (e.g., the embodiments of FIGS. 4a, 4c and 4d), the resilient padding 44 may be provided in addition to formations on the inner surface of the first portion 23.

The padding 44 described above can perform multiple functions. First, it assists in mounting the first portion 23 of the data collection device 20 over the dosage knob 12. In particular, the resilient padding 44 deforms to accommodate the dosage knob 12 within the cavity of the first portion. Friction provides a reactive force in response to insertion of the dosage knob 12 within the first portion 23. This provides tactile feedback to the user indicating that the data collection device 20 is being received over the dosage knob 12. Once the data collection device 20 is installed fully, further movement is prevented. This can be detected by the user through tactile feedback by providing the user with a step change from some relative movement to no relative movement as the proximal end of the dosage knob 12 abuts an abutting surface at the proximal end of the cavity in the first section 23 (see FIG. 6 for instance). The friction between the data collection device 20 and the dosage knob 12 causes the data collection device 20 to remain installed on the injection device 1. This can be achieved without any further mechanism to secure the data collection device 20 to the injection device, although the use of a further mechanism is not precluded. To uninstall the data collection device 20 from the injection device, the friction force needs to be overcome. This can be achieved by applying a strong pulling force, for instance of 30N or more, to the data collection device in the proximal direction.

The padding also provides sufficient engagement for transferring rotation force applied by the user between the first portion 23 and the dosage knob 12 during dose setting/programming.

The force is communicated by friction between the first portion 23 and the dosage knob 12. The friction force acting between the first portion 23 and the dosage knob 12 in the rotational direction exceeds the force required to overcome the forces internal to the drug delivery device 1 by a factor (e.g., of at least 5), or in some implementations, more advantageously at least a factor of 10, which helps to avoid slippage between the components.

As shown schematically in FIG. 4a, the formations 19a-c on the inner surface may take the form of features that have a shape that mates with the shape of the formations 71a, 71b, 71c on the dosage knob 12. For instance, the formations 19a-c on the inner surface may take the form of features that have a shape corresponding closely to the shape of the formations 71a, 71b, 71c on the dosage knob 12. Close correspondence in shape can allow good engagement between the first portion 23 and the dosage knob 12. Where the formations 19a-c on the inner surface have a shape that mates with the shape of the formations 71a, 71b, 71c on the dosage knob 12, the choice of a material with a relatively high friction coefficient to form the inner surface of the first portion 23 contributes to providing a fit between the data collection device 20 and the dosage knob 12 that results in retention of the data collection device 20 on the injection device 1. The optional use of a resilient material on the inner surface of the first portion 23 contributes further to retention of the data collection device 20 on the injection device 1. However, if the fit between the formations on the inner surface of the first portion 23 and the formations 71a, 71b, 71c on the dosage knob 12 is sufficiently close and the coefficient of friction between them is sufficiently high, the material of the inner surface of the first portion 23 need not be resilient.

Figure 4C:
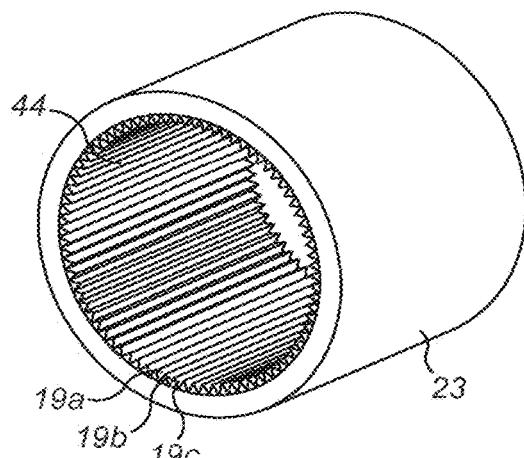

As shown schematically in FIG. 4c, the formations 19a-c on the resilient inner surface of the first portion 23 may take the form of ribs. The ribs may have a triangular cross-section, or they may have a domed cross-section. The ribs may be circumferential. Alternatively, they may be axially arranged. Axial ribs advantageously number at least four times the number of formations 71a, 71b, 71c on the dosage knob 12. This can help to ensure that the formations 71a, 71b, 71c on the dosage knob 12 can easily be received by the formations on the first portion 23 without requiring specific rotational alignment.

Figure 4D:
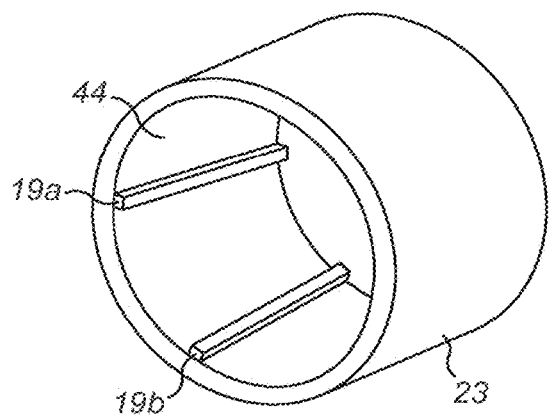

As shown in FIG. 4d, the formations 19a, 19b may take the form of ribs. When the data collection device 20 is placed over the dosage knob 12, the formations 71a-c of the dosage knob fall between the formations/ribs 19a-c of the first portion 23. The formations 19a, 19b here are configured such as to grip the surface of dosage knob 12 between the formations 71a-c when the data collection device 20 is installed fully onto the injection device 1. To this end, the ribs 19a, 19b have a height in the radial direction that is equal to or greater than the radial height of the formations 71 on the dosage knob 12. The ribs are spaced and numbered such that it is unlikely that a proximal end of the ribs will contact a distal end of the formations on the dosage knob 12 when the data collection device is being installed. In particular, the spacing between adjacent ribs may be equal to an integer multiple of the spacing between adjacent formations 71 on the dosage knob 12. The configuration and spacing of the ribs may be such that if there is contact between a proximal end of a rib and a distal end of a formation on the dosage knob 12 when the data collection device is being installed, there is substantially identical contact between multiple ribs and multiple formations 71. When this happens, a small amount of rotational force, which may be provided by the ribs glancing off the formations, causes the ribs to be located between the formations 71 on the dosage knob 12.

The ribs may or may not be twisted with respect to the longitudinal axis of the data collection device 20. In particular, there may be a relative twist between different formations 19a-c, for instance one formation/rib 19a has a clockwise twist and the next formation/rib 19b has an counterclockwise twist. When the data collection device 20 is placed over the dosage knob 12, the formations 71a-c of the dosage knob fall between the formations/ribs 19a-c of the first portion 23.

In various arrangements, the first portion 23 is shaped such that there is substantially even engagement between the first portion 23 and the dosage knob 12 for the whole of the axial length of the dosage knob 12. This helps to ensure correct axial orientation of the data collection device 20 with the injection device 1. Axial orientation is provided because the shapes of the components are such that any incorrect orientation results in a corrective force being applied radially between the dosage knob 12 and the first portion 23 as they are mated together. Correct axial alignment is useful because it provides a better transmission of rotation force from the first portion 23 to the dosage knob 12 and because it provides better feedback to the user when dose delivery is performed. It also generally improves the experience of the user.

In some embodiments, the first portion 23 may be formed with a rigid section surrounding at least part of the second portion 24 and a resilient section that surrounds at least part of the dosage knob 12, the rigid section providing a firm gripping surface for the user when mounting or removing the data collection device 20 onto or from the injection device 1 and the resilient section assisting in mounting the first portion 23 over the dosage knob 12 and providing sufficient engagement for transferring rotation between the first portion 23 and dosage knob 12 during programming and medicament expulsion. Optionally, the rigid section may be formed of a different material from the resilient section. Such a first portion 23 may, optionally, also include formations 19a-c configured to co-operate with the formations 71a, 71b, 71c on the dosage knob 12, as described above, and/or resilient padding 44.

In some embodiments, an indicator is provided on the data collection device. The indicator may for instance be a groove, a nose or a printed feature. The indicator facilitates alignment by the user of the data collection device with a nose of the injection device 1. However, in some embodiments (e.g., in the embodiments shown in the drawings), no such alignment is needed.

The coupling between the first portion 23 and the dosage knob 12 may include no moving parts. The first portion 23 is coupled with the dosage knob 12 solely through a close fit, through friction between surfaces of the components, optionally assisted by deformation of a resilient material forming the coupling surface of the first portion 23.

To set a medicament dosage amount to be administered, the user may grip and rotate the first portion 23, since this will cause the dosage knob 12 of the injection device 1 to turn and, thereby, program the dosage amount.

Also, in this particular example, the second portion 24 is a body located within the first portion 23, to which it is rotatably attached using bearings 25. The second portion 24 includes an outer portion 26, which includes the endplate 22 and optionally a display 22a. The second portion 24 also includes an inner portion 27. When the data collection device 20 is attached to the injection device 1, the inner portion 27 overlies the injection button 11. The outer portion 26 and the inner portion 27 are attached by a fixture 28 that prevents rotation relative to each other. However, in this embodiment, the outer portion 26 can be moved axially relative to the inner portion 27 and one or more resilient members, such as springs 29, may be provided to bias the outer portion 26 away from the inner portion 27.

The data collection device 20 is configured to detect axial movement of the outer portion 26 relative to the inner portion 27. Movement greater than a predetermined amount may be detected using a switch 53, for instance, as is described in more detail below.

In this particular arrangement, first electrical contacts 30 are provided on the outer portion 26, while corresponding second electrical contacts 31 are provided on the inner portion 27. When a user presses the endplate 22, the outer portion 26 moves axially towards the inner portion, establishing a connection between the first and second electrical contacts 30, 31. Further pressure on the endplate 22 causes the inner portion 27 to press against, and activate, the injection button 11. The first and second electrical contacts 30, 31 provide a data connection between the processor arrangement 50 and display 22a when engaged.

Figure 5:
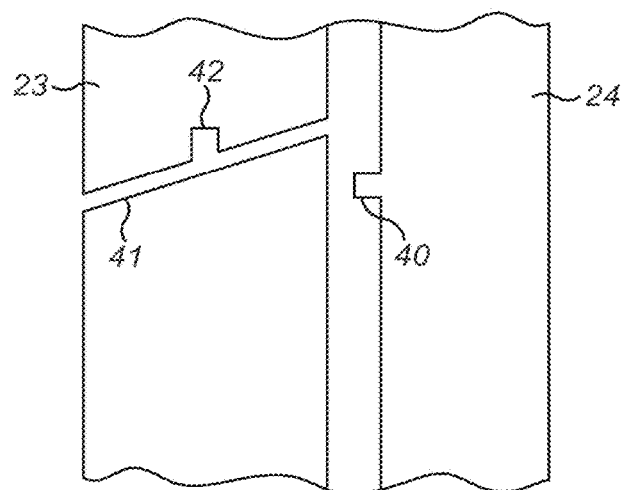
FIG. 5 depicts example locking formations on the data collection device of FIG. 2.

Optionally, the data collection device 20 may be arranged to have a first configuration, in which rotation of the first portion 23 relative to the second portion 24 is prevented, and a second configuration, in which such rotation is unimpeded. For example, as shown in FIG. 5, the first portion 23 and the second portion 24 may be provided with lock formations such as a protrusion 40 on one of the first and second portions 23, 24 and a circumferential groove 41 and axial recess 42 on the other of the first and second portions 23, 24. In this particular example, in the first configuration, the protrusion 40 is located in the recess 42 and rotation is prevented. The data collection device 20 may be switched to the second configuration by axial movement of the second portion 24 relative to the first portion 23, so that the protrusion 40 is located within the circumferential groove 41 and rotation is permitted.

While the arrangement shown in FIG. 5 includes lock formations in the form of a protrusion 40, groove 41 and recess 42, other types of co-operating formations or lock methods may be used to prevent rotation in the first configuration.

Figure 6:
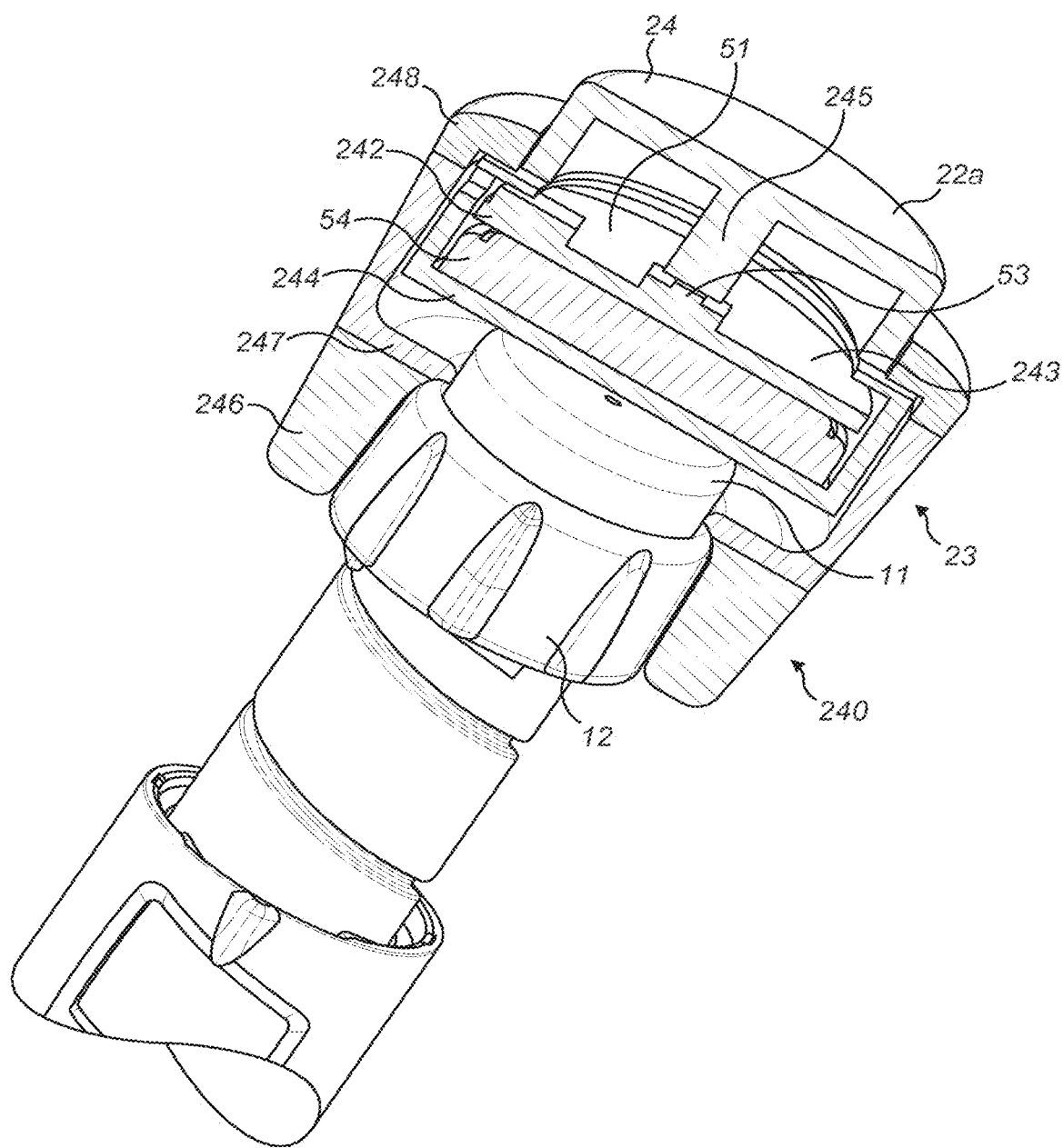
FIG. 6 is an isometric cutaway view of a first variation of the data collection device of FIG. 2.

FIG. 6 is an isometric cutaway view of a first alternative data collection device 240, which is a variation of the data collection device 20.

Figure 7A:
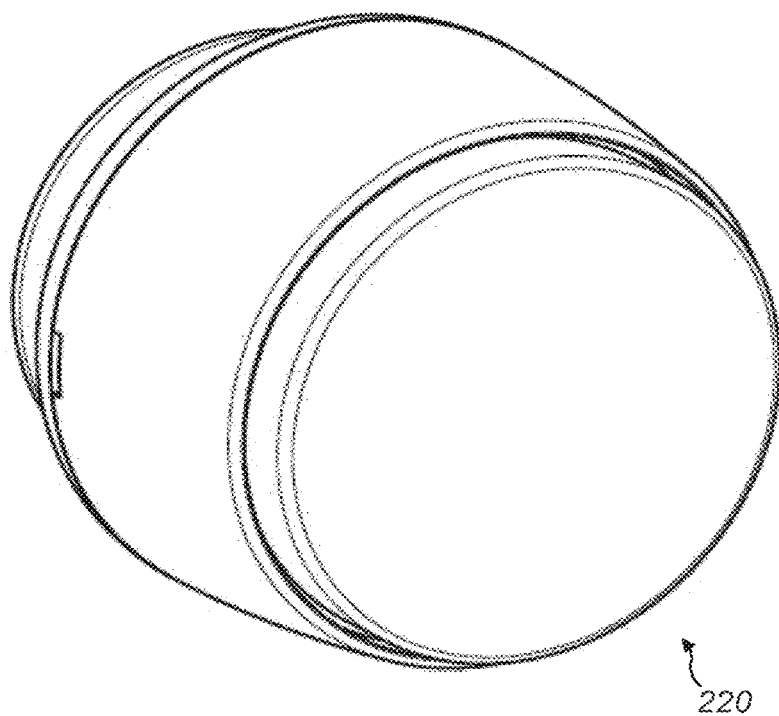
FIG. 7*a* is a proximal end isometric view of a second variation of the data collection device of FIG. 2.

FIGS. 7a to 7e are different views of a second alternative data collection device 220, which is another variation of the data collection device 20. FIG. 8 is a cross-sectional view of the second alternative data collection device 220 installed on the injection device.

In these Figures, reference numerals are retained from FIG. 2 for like elements. Unless otherwise stated or unless impossible, features of the FIG. 2 device are present in the FIGS. 6-8 data collection devices. Also, features of any one device are present in all of the other devices.

The FIGS. 2, 5, 6, 7 and 8 data collection devices have a common characteristic that the first portion 23 has a larger accessible surface area than does the second portion 24.

The data collection device 240 of FIG. 6 includes a capsule 244, which is contained within the body of the data collection device 240. The capsule 244 itself contains a power source 54 or battery, in the form of a coin cell in this example, and a printed circuit board (PCB) 242. Mounted on the PCB are a number of electronic components including a communications interface 243, for instance a Bluetooth™ Low Energy chip or a Near Field Communications (NFC) chip. It also supports a switch 53 for detecting axial movement of the second portion 24. The PCB 242 further supports a sensor arrangement 51, which is configured to detect rotation of the first portion 23 relative to the second portion 24. In particular, the capsule 244 is fixed in rotation relative to the second portion 24 and rotates with the second portion 24 relative to the first portion 23 when the dose is being delivered.

The power source 54 provides power to the electronic components of the data collection device 240. The power source 54 is located distally to the PCB 242. The power source 54 is abutted by the distal end of the capsule 244 and by the PCB 242.

The first portion 23 has three key structural elements. The first portion 23 may be formed as one part, or it may be formed of multiple parts that are connected together. A first element 246 of the first portion 23 is configured to engage with the dialing knob 12. Aspects of the first element are described above, especially in relation to FIGS. 4a to 4d. A second element 246 is configured to engage with the dose delivery button 11. In particular, the second element 246 is configured to fit closely around the dose delivery button 11. The second element 246 helps to ensure correct axial alignment of the data collection device 240 on the injection device 1. The second element 246 may take the form of a ring. The second element 246 may have a low friction inner surface, so as not to impede movement of the dose delivery button 11 in the distal direction. The third element 248 is located at the proximal end of the first portion 23. The third element 248 extends radially inwardly. It also surrounds the second portion 24 in the radial direction.

The capsule 244 is movable in the axial direction within the cavity formed in the first portion 23. The capsule 244 is restrained in the proximal direction at the periphery of the capsule 244 by the third element 248 of the first portion 23. In the distal direction, the capsule 244 abuts the dose button 11.

The second portion 24 is connected at its periphery to a proximal end of the capsule 244. A pillar 245 is provided at the center of the second portion 24 and extends axially. The pillar 245 is coincident with the switch 53, and may or may not contact it when no force in the distal direction is applied to the second portion 24. The center of the second portion 24 is slightly deformable in the distal direction.

The switch 53 is configured to be operated upon movement of at least part of the second portion 24 relative to the first portion 23. A force required to operate the switch 53 may be lower than a force required to cause medicament delivery from the injection device 1. By using operation of the switch 53 to trigger powering of components of the data collection device, the components of the data collection device will thus be powered before dose delivery commences. For instance, the force required to operate the switch 53 may be about 2 N, or more generally between 1 and 5 N.

Operation of the data collection device 240 will now be described. First, a user dials a dose into the injection device 1. This is achieved by the user rotating the first portion 23 of the data collection device 240. The rotational force is communicated to the dosage knob 12, which rotates also. The second portion 24 also rotates along with the first portion when the dose is being dialed. During dialing, the electronics on the PCB 242 are not powered.

Once the user has dialed the desired dose, they press the second portion 24 in order to start delivery of the dose, i.e. to cause injection. Initially, the second portion 24 deforms slightly and the center of the second portion 24 moves in the distal direction more than the periphery of the second portion 24. In other words, the center of the second portion 24 moves axially relative to the periphery of the second portion and axially relative to the first portion. This causes the pillar 245 to activate the switch 53. This causes the electronics on the PCB 242 to be powered and thus activated. Further movement of the second portion 24 is communicated into movement of the capsule 244 within the first portion 23. This is communicated to movement of the dose button 11 in the distal direction. Once the dose button 11 has moved enough to permit dose delivery (which occurs by causing disengagement of a clutch, not shown, within the injection device 1), the dosage knob 12 begins to rotate relative to the dose button 11 as the dose delivery button is moved in the distal direction by action of the user. In particular, the dose delivery button 11 does not rotate relative to the housing 10 of the injection device 1, but the dosage button and the number sleeve 70 move helically (i.e. they move axially and rotate simultaneously). The first portion 23 thus rotates relative to the second portion 24. When the user ceases to press on the second portion 24, or when all of the dose is delivered, rotation of the first portion 23 relative to the second portion 24 ceases. The amount of rotation that occurs indicates the delivered dose. The amount of rotation is detected by the sensor 51, and this is used to calculate the delivered dose. The delivered dose is then stored in memory, as described below.

The FIG. 6 data collection device is absent of a display, although a display for displaying a delivered dose may be provided.

Instead of the display, the FIG. 6 data collection device includes an optical indicator arrangement. For instance, the optical indicator arrangement may be one or two light sources, such as light emitting diodes (not shown). The optical indicator arrangement may be provided axially or peripherally on the proximal end face of the second portion 24, or on the circumference of the second portion 24 or the first portion 23, for instance.

The optical indicator arrangement is configured to provide feedback regarding a dwell period. When the injection finishes, which is detected by detecting the ceasing of rotation between the first and second portions 23, 24 or the ceasing of operation of the switch 53, the optical indicator arrangement of the data collection device indicates that a dwell time period is in place. For instance, the optical indicator arrangement starts blinking, (e.g., the optical indicator arrangement is activated intermittently). The frequency of blinking can change over the dwell period. For instance, at the start of the dwell period the frequency may be about 5 Hz and at the end of the period the frequency may be about 1 Hz. When the dwell period is finished, the optical indicator arrangement may remain illuminated, to indicate the end of the sequence and the end of the dwell period.

The duration of the dwell period depends on the type of medicament. The type of medicament or the dwell time may be communicated to the data collection device, for instance from a mobile phone running an application that is configured to operate in conjunction with the data collection device.

The optical indicator arrangement is configured to provide feedback regarding a medicament dose having already been taken recently. When the user presses the second portion 24 of the data collection device, the data collection device checks a time at which the last dose was delivered. The user may press the second portion 24 of the data collection device in order to initiate delivery of medicament or specifically to request information about the time since the last dose delivery. The data collection device determines if the dose already taken notification is to be provided by observation of the switch 53, a current time and a time of the last dose delivery. If it is determined that no significant dose (e.g. larger than 2 units) was delivered in a certain time period, for instance the previous hour, the optical indicator arrangement indicates that delivery of medicament is permitted. For instance, the optical indicator arrangement may glow green for one second. If instead it is determined that a significant dose was delivered within the certain time period, the optical indicator arrangement may glow or flash an alert, for instance red in color.

The optical indicator arrangement is configured to provide feedback regarding end of life of the data collection device. When an error or another unsolvable issue such as an empty battery is detected, the data collection device indicates this, for instance by operating the optical indicator arrangement to blinking in red for at least several hours.

Once the user removes the distally directed force from the second portion, spring force from within the injection device causes the dose button 11 to return the capsule 244 and the second portion 24 to the original position.

The data collection device 220 of FIG. 7 is very similar to the data collection device of FIG. 6. However, a different mechanism retains the second portion 24 in the distal direction. The injection device 1 is absent from FIGS. 7a to 7e, but is shown in FIG. 8.

Figure 7B:
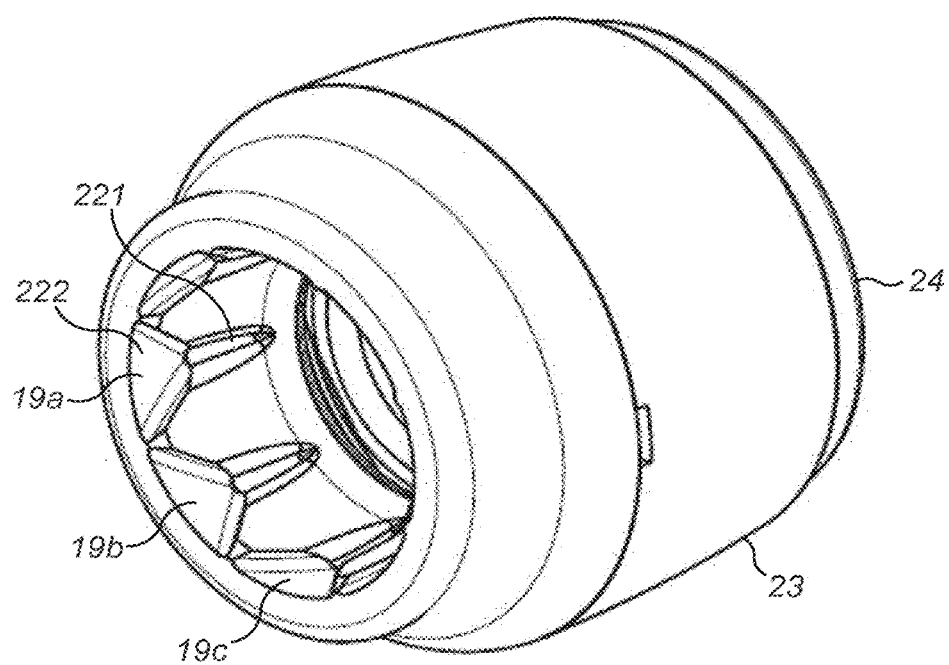
FIG. 7*b* is a distal end isometric view of the second variation of the data collection device of FIG. 2.
Figure 7C:
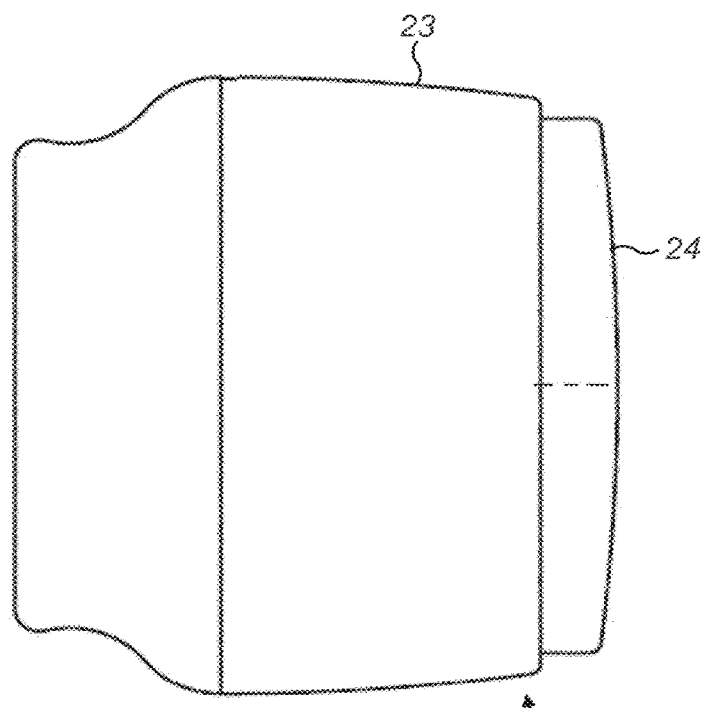
FIG. 7*c* is a side view of the second variation of the data collection device of FIG. 2.
Figure 7D:
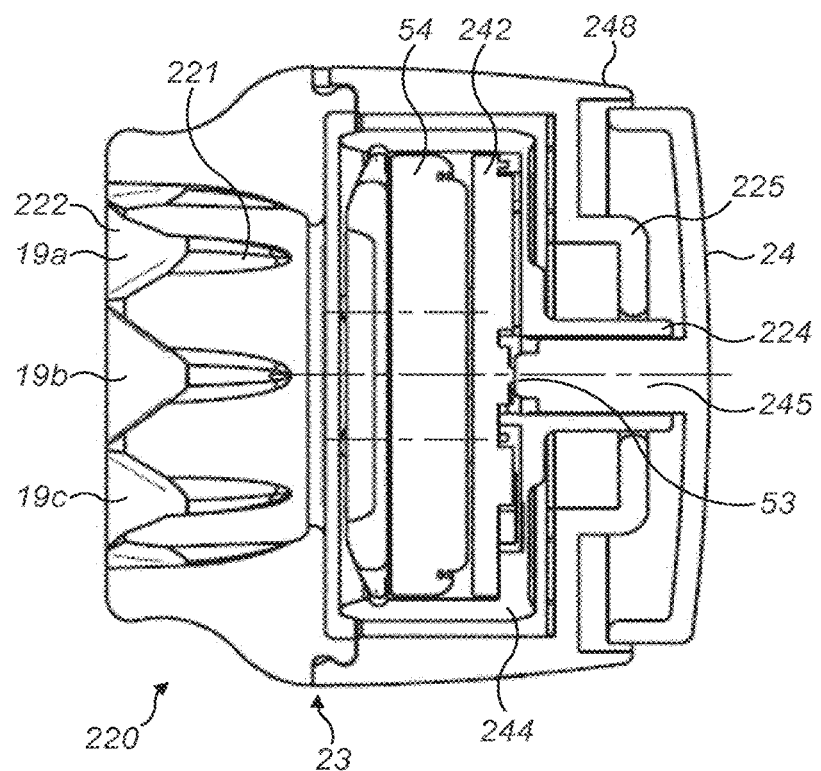
FIG. 7*d* is a side cross-section view of the second variation of the data collection device of FIG. 2.
Figure 8:
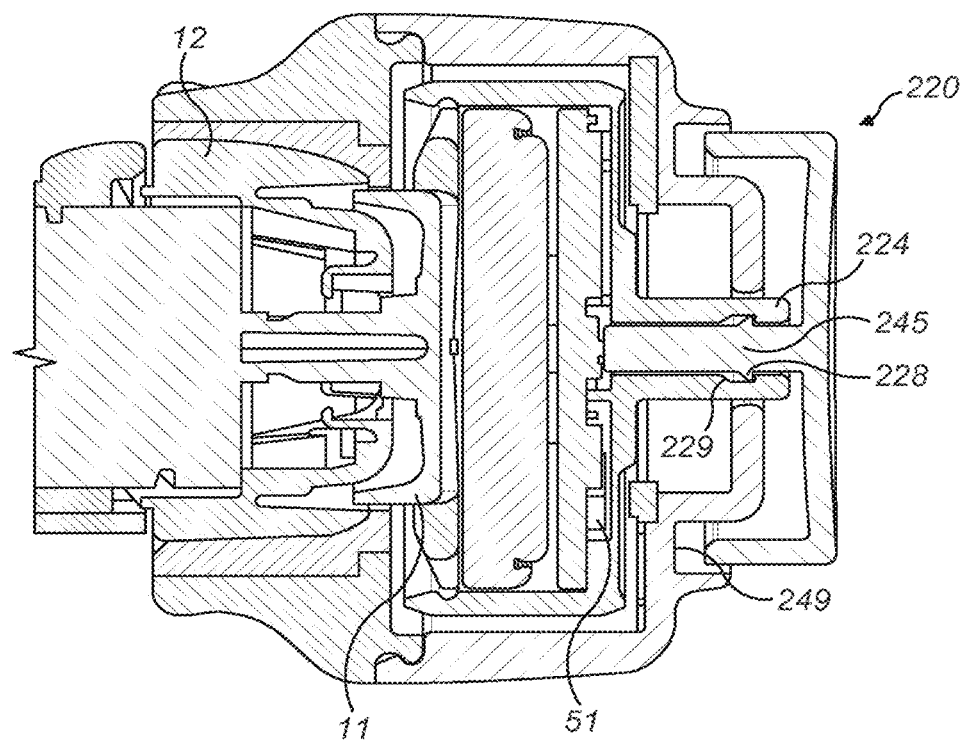
FIG. 8 is a cross-sectional view of the second variation of the data collection device of FIG. 2 installed on the injection device of FIG. 1.

In FIGS. 7b and 7d, the formations 19a-c are shown clearly. It will be seen that the formations have two main parts. A proximally located part 221 is a recess having a shape that corresponds well with the shape of the corresponding formation 17 on the dosage knob 12 in every dimension. A distally located part 222 has a mouth that flares outwardly in the distal direction. The mouth of the part 222 serves to catch the proximal end of a formation 17 of the dosage knob 12 as the data collection device 240 is placed onto the injection device 1. The sides of the mouth then cause adjustment of the rotational alignment so that the formations 17 on the dosage knob 12 are guided into the proximally located part 221 of the formations 19a-c of the first portion 23. When fully installed, the distally located part 222 of the formations 19a-cc on the first portion 23 are engaged in the radial direction with the formations 17 on the dosage knob 12. This helps to keep correct axial alignment of the data collection device 220 on the injection device 1 and helps to retain the data collection device 220 on the injection device through friction.

Although described particularly with reference to FIGS. 7a and 7d, the configuration and operation of the formations 19 may be the same on all of the data collection devices embodied in this specification.

The second portion 24 includes the pillar 245. The third element 248 of the first portion 23 includes a radially inwardly extending collar 225. The capsule 244 includes an annular neck portion 224. The neck portion 224 fits around the pillar 245 in a rotationally locked connection. The pillar 245 can move in the distal direction relative to the capsule 244 by a small amount, to activate the switch 53 as the dose delivery procedure is commenced, but before dose delivery starts, but otherwise is not movable relative to the capsule 244.

The pillar 245 and the neck portion 224 have interoperating features that limit axial movement of the components relative to each other. In particular, one or more protrusions 228 fit into one or more indents 229. The movement of the second portion 24 relative to the capsule 244 is limited by the ends of the one or more indents 229 as regards the one or more protrusions 228. In this example, the protrusions 228 are provided on the pillar 245 and the indents 229 are provided on the neck portion 224, but alternative arrangements will be envisaged by a person skilled in the art.

A low friction surface is provided between the radially inward end of the collar 225 and the radially outward surface of the neck 224. Thus, the first portion 23 and the capsule 244 are able to rotate relative to one another during dose delivery. The second portion 24 is rotatably coupled with the first portion at a location that is closer radially to the longitudinal axis of the data collection device 240 than it is to the outer diameter of the data collection device. The provision of the contact surfaces of the first portion 23 and the capsule 244/second portion 24 at a relatively radially inward positon is advantageous. In particular, it reduces the area of contact, which thus reduces friction. Thus, less torque is required to rotate the first portion 23 and the second portion 24 relative to one another during dose delivery. This improves drug delivery and makes the combination of the injection device 1 and the data collection device 220 easier to use.

Figure 7E:
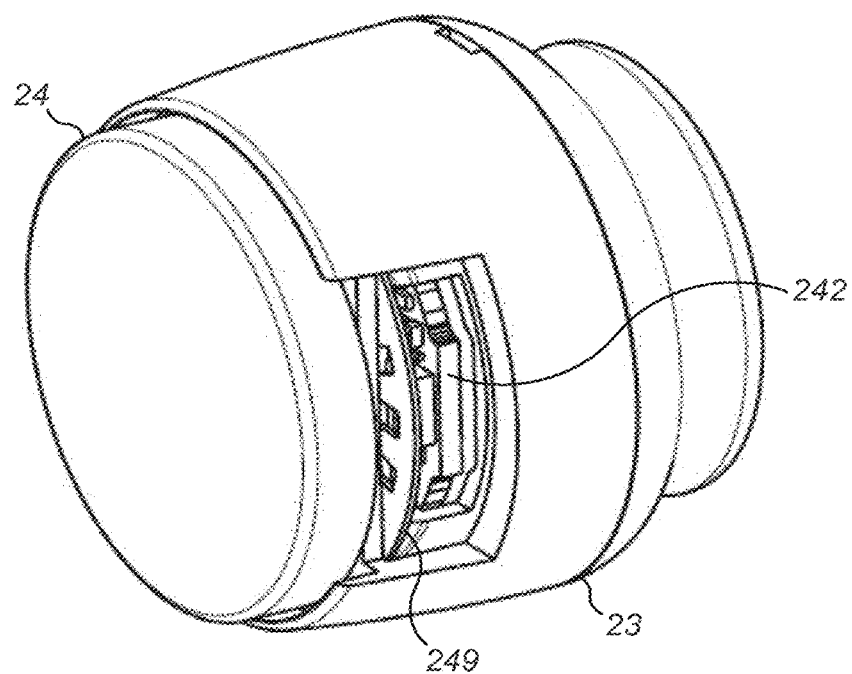
FIG. 7*e* is a partial cutaway isometric proximal view of the second variation of the data collection device of FIG. 2.

A slotted disc 249, visible in FIG. 7e, allows the sensor 51 to detect the amount of rotation of the first portion 23 relative to the second portion 24. In particular, a photodiode or other optical sensor 51 on one portion, for instance the second portion 24, is directed at the slotted disc 249, which rotates with the other portion, for instance the first portion 23. The sensor 51 detects light which is reflected or transmitted by an amount that varies according to the position of the slots relative to the sensor 51 as the slotted disc 249 moves. Rotation of the slotted disc 249 relative to the sensor 51 thus causes the signal detected by the sensor to change.

There are two main alternatives for using the sensor output to determine the amount of rotation. First, the number of high intensity or low intensity pulses can be counted, to derive the amount of rotation. High or low intensity pulses can be detected for instance using a threshold circuit. Alternatively, the number of changes from low intensity to high intensity, or vice versa, can be counted. Changes can be determined using a differentiator circuit, for instance. Counting the number of changes provides good reliability because it does not depend on a correct intensity threshold being used. In either case, the number of slots passing the sensor 51 is counted, and therefrom the dose delivered can be calculated.

The FIGS. 7 and 8 data collection device is absent of a display, although a display for displaying a delivered dose may instead be provided.

Operation of the data collection device 220 of FIGS. 7 and 8 will now be described. First, a user dials a dose into the injection device 1. This is achieved by the user rotating the first portion 23 of the data collection device 220. The rotational force is communicated to the dosage knob 12, which rotates also. The second portion 24 also rotates along with the first portion when the dose is being dialed. During dialing, the electronics on the PCB 242 are not powered.

Once the user has dialed the desired dose, they press the second portion 24 in order to start delivery of the dose, i.e. to commence injection. Initially, the second portion 24 moves in the distal direction from one end to the other end of the distance permitted by interoperation of the one or more protrusions 228 fit into one or more indents 229. At or close to the limit of travel, the location of the second portion 24 activates the switch 53. This causes the electronics on the PCB 242 to be powered and thus activated. Further movement of the second portion 24 is communicated into movement of the capsule 244 within the first portion 23. This is communicated to movement of the dose button 11 in the distal direction. Once the dose button 11 has moved enough to commence dose delivery, the dosage knob 12 begins to rotate relative to the rest of the injection device 1, including the dose button 11. The first portion 23 thus rotates relative to the second portion 24. When the user ceases to press on the second portion 24, or when all of the dose is delivered, rotation of the first portion 23 relative to the second portion 24 ceases. The amount of rotation that occurred indicates the delivered dose. The amount of rotation is detected by the sensor 51, and this is used to calculate the delivered dose. The delivered dose may then be displayed on the display 22a and/or stored in non-transient memory or transient memory, which may or may not be part of the processor arrangement.

Once the user removes the distally directed force from the second portion, spring force from within the injection device causes the dose button 11 to return the capsule 244 and the second portion 24 to the original position.

FIGS. 9a to 9e are different views of a third alternative data collection device 120, which is a variation of the data collection device 20.

FIGS. 10a to 10d are different views of a fourth alternative data collection device 140, which is a variation of the data collection device 20.

In these Figures, reference numerals are retained from FIGS. 2, 6, 7 and 8 for like elements. Unless otherwise stated or unless impossible, features of the FIGS. 2, 6, 7 and 8 data collection devices are present in the FIGS. 9 and 10 data collection devices. Also, features of any one device are present in all of the other devices unless otherwise stated.

The FIGS. 9 and 10 data collection devices have a common characteristic that the second portion 24 has a larger user-contactable external surface area than does the first portion 23.

Figure 9A:
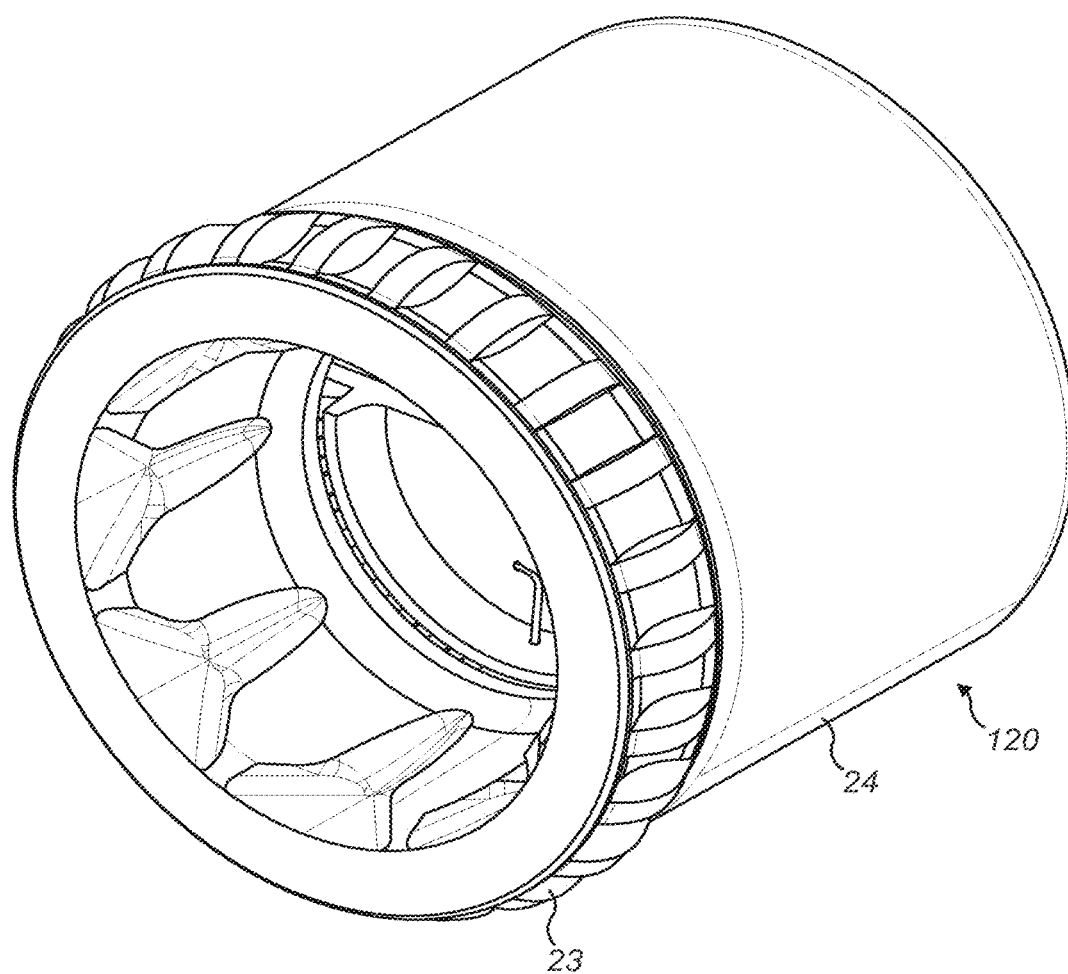
FIG. 9a is a distal end isometric view of a third variation of the data collection device of FIG. 2.
Figure 9B:
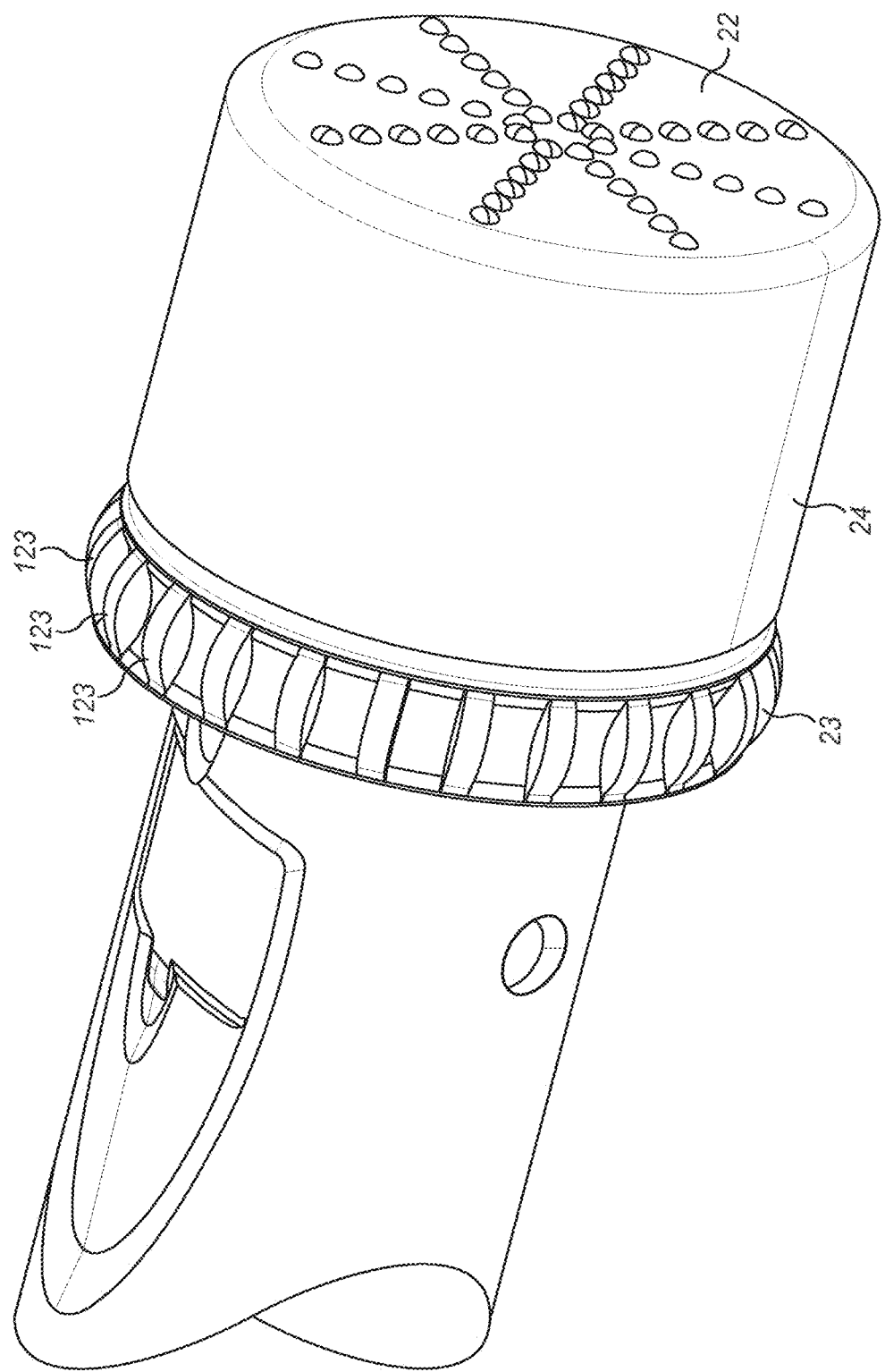
FIG. 9b is a proximal end isometric view of the third variation of the data collection device of FIG. 2 installed on the injection device of FIG. 1.
Figure 9C:
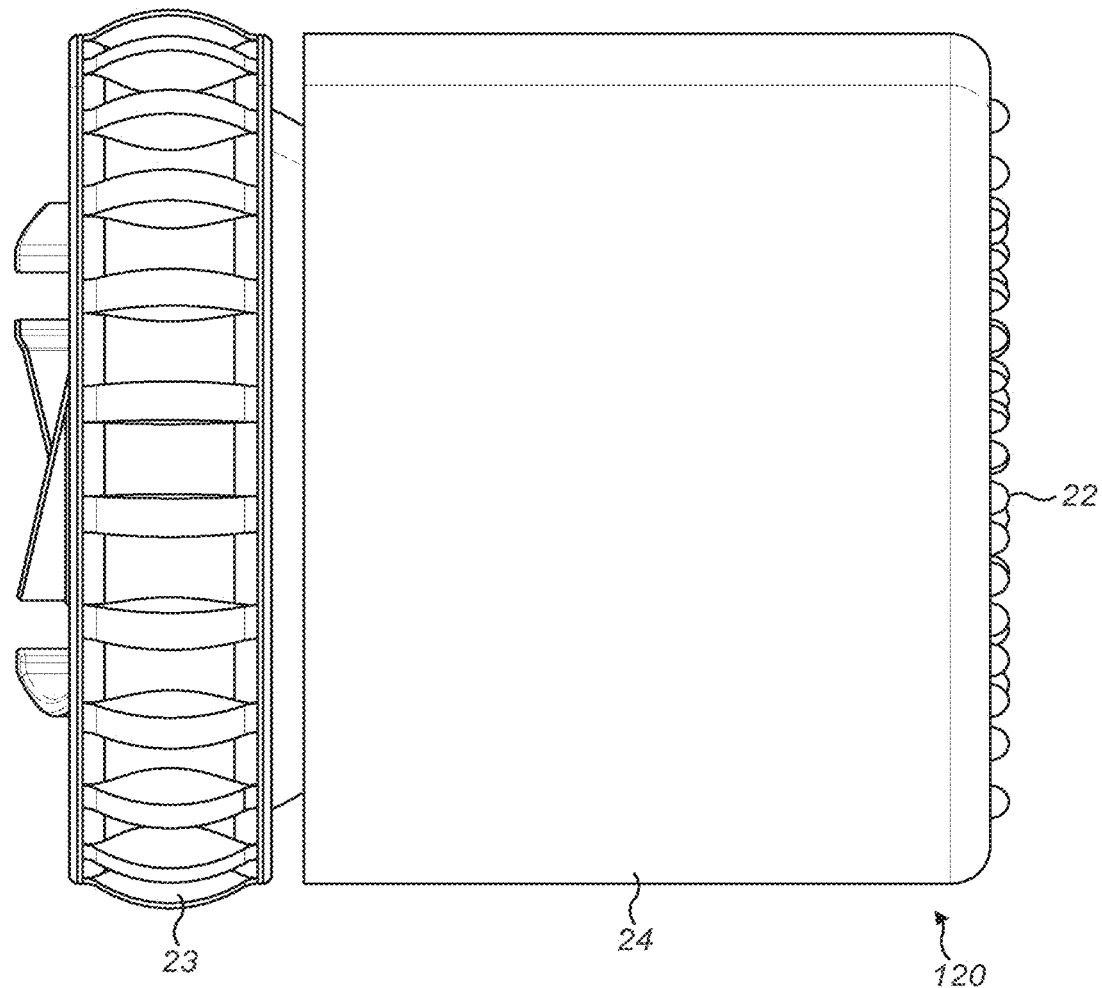
FIG. 9c is a side view of the third variation of the data collection device of FIG. 2.
Figure 9D:
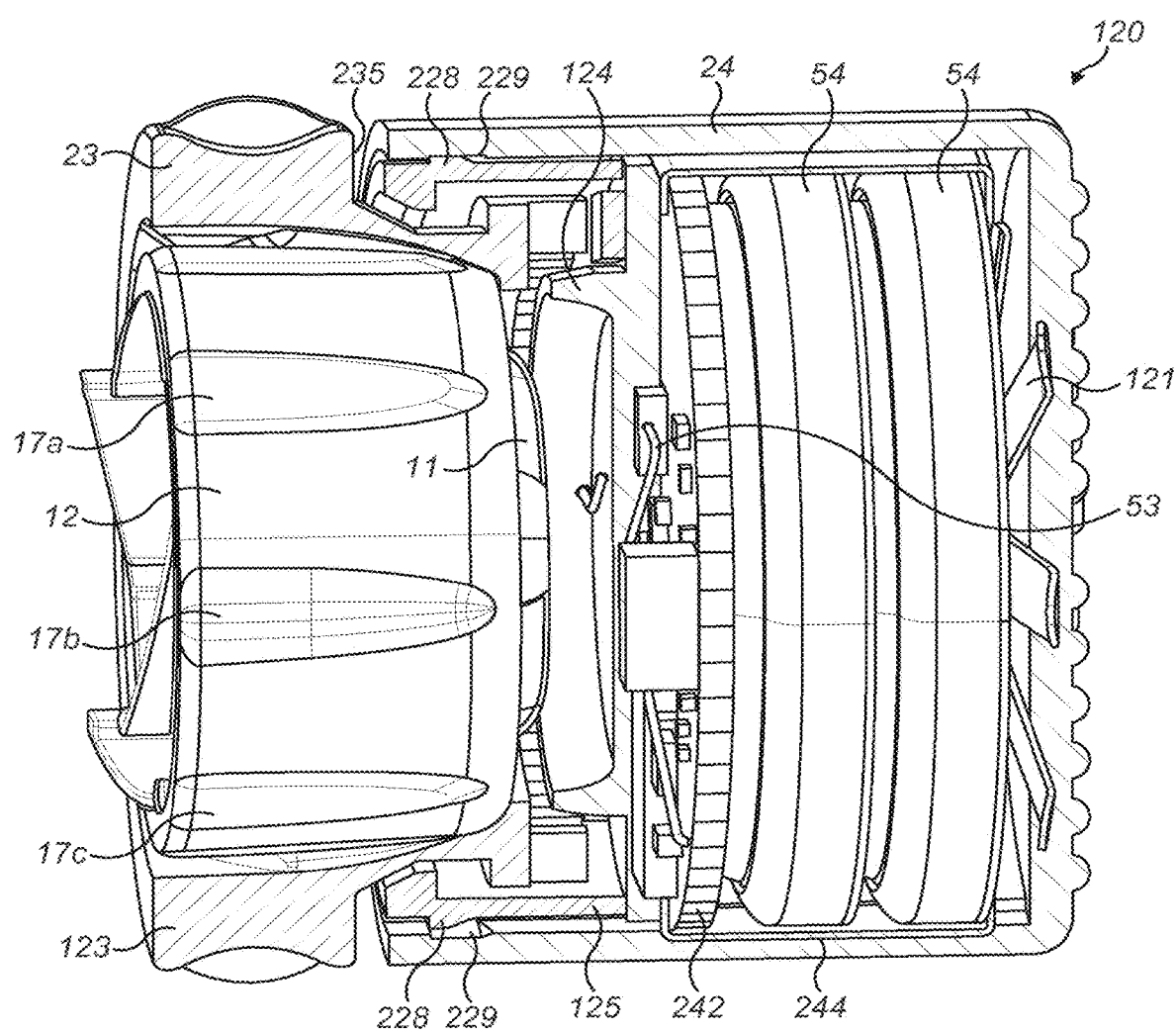
FIG. 9d is a cutaway side view of the third variation of the data collection device of FIG. 2.
Figure 9E:
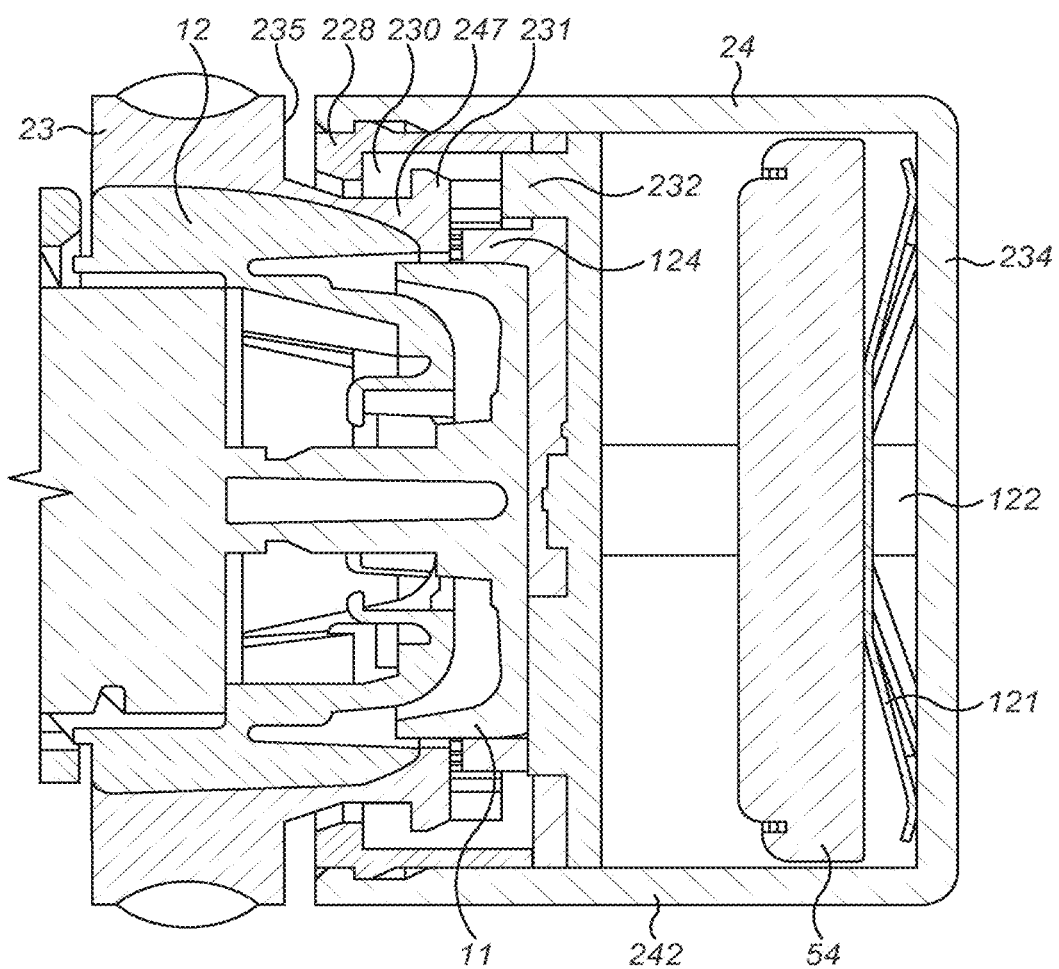
FIG. 9e is a side cross-section view of the third variation of the data collection device of FIG. 2.

The shape of the second element 247 of the first portion 23, which serves to guide the data collection device to correct axial alignment using the dose button 11, is clearly visible in FIGS. 9a and 9e. The dose button 11 is shown in a depressed state in FIG. 9a, so it is not shown engaging the second element 247 of the first portion 23 in this Figure. Second element 247 is shaped such that it at least partly fits around a dose button of the injection device when the data collection device is coupled to the injection device.

In the FIG. 9 data collection device 120, the second portion 24 is relatively large. Within the second portion 24, a spring 121 biases two power source (e.g. batteries) 54 against the distal face of the PCB 242. A conductor 122 forms an electrical circuit between the proximal face of the proximal power source 54 and the PCB 242. The switch 53 is formed on the proximal face of the PCB 242. The switch 53 may include a spring terminal, as shown in the Figure. The spring terminal is moved, thereby to operate the switch 53, upon movement of the second portion 24 in the distal direction relative to the first portion 23. A force required to operate the switch 53 is lower than the force required to cause medicament delivery from the injection device 1. By using operation of the switch 53 to trigger powering of components of the data collection device, the components of the data collection device will thus be powered before dose delivery commences. For instance, the force required to operate the switch 53 may be about 2 N, or more generally between 1 and 5 N.

A first collar 124 is directed in a distal direction from the distal end of the capsule 244. A second collar 125 extends distally from the distal end of the capsule 244. The second collar 125 is outside of the first collar 124, and they are concentric.

The second collar 125 and the second portion 24 have interoperating features that limit axial movement of the components relative to each other. In particular, one or more protrusions 228 fit into one or more indents 229. The movement of the second portion 24 relative to the capsule 244 is limited by the ends of the one or more indents 229 as regards the one or more protrusions 228. In this example, the protrusions 228 are provided on the second collar 125, and thus the capsule 244, and the indents 229 are provided on the second portion 24, but alternative arrangements will be envisaged by a person skilled in the art.

The first collar 124 snugly fits the dose button 11, to assist in axial alignment between the data collection device 120 and the injection device 1 during delivery. A washer (not shown) may be provided between the first collar 124 and the dose button 11, to improve contact between the components. The first collar 124 does not contact the first portion 23 during installation of the data collection device 120 nor during dose delivery.

The first portion 23 is provided with grip features 123. These allow a user to grip the first portion so as to provide torque and thus rotate the first portion when setting a dose. The grip features 123 provide surfaces that extend generally radially, to which the user can provide force to cause rotation of the first portion 23.

As can be seen best from FIG. 9e, the first portion 23 is coupled to the second portion 24 by a connector arrangement 230, 231, 228. In particular, the first portion 23 includes a first L section component 231, which has an abutting surface facing in the distal direction. This is formed as part of the first portion 23. A second L section component 230, forming part of the second portion 24, is coupled to a support 232, which is coupled to the PCB 242, the first collar 124 and other components of the second portion 24. The second L section component 230 has an abutting surface facing in the proximal direction. The second L section component 230, and the other components that are coupled to it, are attached to the first section 23 during manufacture by application of a force to cause a snap fit such that the abutting surfaces of the first and second L section components 231, 230 are located together. The snap fitting of the second L section component 230 over the first L section component 231 is facilitated by a sloping face of the first L section component 231, which faces slightly in the proximal direction.

After the power source 54 has been included within the second section 24, the main body 234 of the second portion, with the third L section component 228 already fitted, is snap fitted over the second L section component 230. The snap fitting is facilitated by a sloping face of the third L section component 228, which faces slightly in the distal direction. A proximally facing abutting surface of the third L section component then abuts a distally facing abutting surface of the second L section component 228. This arrangement keeps the spring 121 in compression, thereby ensuring good electrical connection of the power source 54. It also allows for a simple manufacturing process and the use of low cost components.

Once the first portion 23 is fitted to the second portion 24, the two portions rotate relative to one another by a low friction contact between surfaces of the first and second L section components 230, 231. The low friction contact may be provided by suitable coating of the relevant surfaces, or by suitable material choice of the components themselves.

During installation of the data collection device 120 on the injection device 1, force is applied in an axial direction. During installation, the user is likely to apply force to the second portion 24. In this case, the force is communicated to the first portion, to result in fitting of the first portion 23 over the dosage knob 12, by the distal end of the third L section component 228, or more generally the main body 234, against a proximally facing surface 235 of the first portion 23. A spring force provided by the data collection device 120 forces the second portion 24 in the proximal direction relative to the first portion 23, after installation. This spring force is greater than a reaction force that is provided by the injection device 1 during dose delivery (the reaction force results primarily from friction from movement of internal components and hydrodynamic force resulting from medicament expulsion through the needle). Thus, the distal end of the third L section component 228, or more generally the main body 234, does not contact the proximally facing surface 235 of the first portion 23 during dose delivery. If they were to be in contact during dose delivery, a friction force would oppose rotational movement between the first portion 23 and the second portion 24.

The FIG. 9 data collection device 220 is absent of a display, although a display for displaying a delivered dose may instead be provided.

Operation of the data collection device 220 of FIG. 9 will now be described. First, a user dials a dose into the injection device 1. This is achieved by the user rotating the first portion 23 of the data collection device 220. The rotational force is communicated to the dosage knob 12, which rotates also. The second portion 24 also rotates along with the first portion when the dose is being dialed. During dialing, the electronics on the PCB 242 are not powered.

Once the user has dialed the desired dose, they press the second portion 24 in order to start delivery of the dose, i.e. to cause injection. Initially, the second portion 24 moves in the distal direction from one end to the other end of the distance permitted by interoperation of the one or more protrusions 228 and the one or more indents 229. At or close to the limit of travel, the location of the second portion 24 activates the switch 53. This causes the electronics on the PCB 242 to be powered and thus activated. Further movement of the second portion 24 is communicated into movement of the capsule 244 in the distal direction. This is communicated to movement of the dose button 11 in the distal direction. Once the dose button 11 has moved enough to commence dose delivery, the dosage knob 12 begins to rotate relative to the rest of the injection device 1, including the dose button 11. The first portion 23 thus rotates relative to the second portion 24. When the user ceases to press on the second portion 24, or when all of the dose is delivered, rotation of the first portion 23 relative to the second portion 24 ceases. The amount of rotation that occurred indicates the delivered dose. The amount of rotation is detected by the sensor 51, and this is used to calculate the delivered dose. The delivered dose may then be displayed on the display 22a.

Once the user removes the distally directed force from the second portion, spring force from within the injection device causes the dose button 11 to return the capsule 244 and the second portion 24 to the original position.

Because the first portion 23 is relatively small and because no part of the first portion is near to the proximal face of the second portion 24, the user is easily able to avoid contacting the first portion 23 when using the second portion 24 to cause dose delivery. This is the same regardless of whether the user uses their thumb or their index finger to manipulate the second portion 24.

The FIG. 10 data collection device 140 is very similar to the FIG. 9 data collection device 120.

One main difference is that the data collection device 141 includes a grip element 141 formed of a high friction material, instead of macro features 123, to provide a grip by which the user can dial a dose into the injection device. The grip element 141 is in the form of a band. The grip element is fitted into a groove 142 that is provided on the outside surface of the first portion 23.

Another main difference is that the data collection device 140 is generally conical shaped. The diameter of the data collection device 140 is greater at the proximal end than it is at the distal end. This further facilitates the user being able to avoid contacting the first portion 23 when using the second portion 24 to cause dose delivery. This is the same regardless of whether the user uses their thumb or their index finger to manipulate the second portion 24.

Figure 10A:
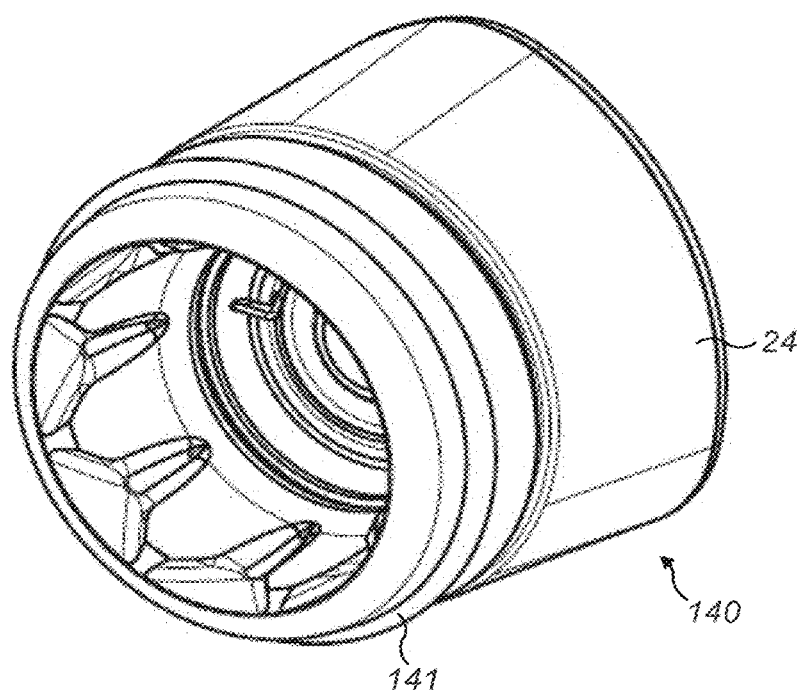
FIG. 10a is a distal end isometric view of a fourth variation of the data collection device of FIG. 2.
Figure 10B:
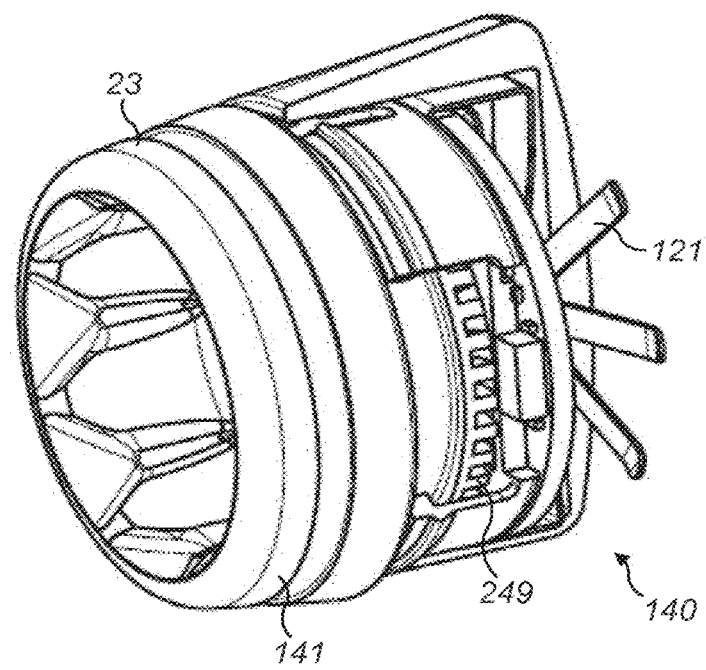
FIG. 10b is a distal cutaway view of the fourth variation of the data collection device of FIG. 2.
Figure 10C:
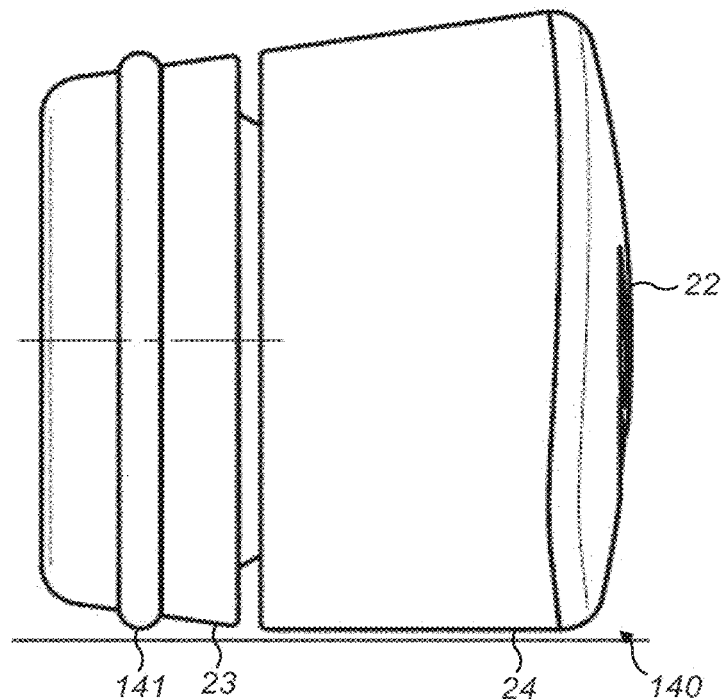
FIG. 10c is a side view of the fourth variation of the data collection device of FIG. 2.
Figure 10D:
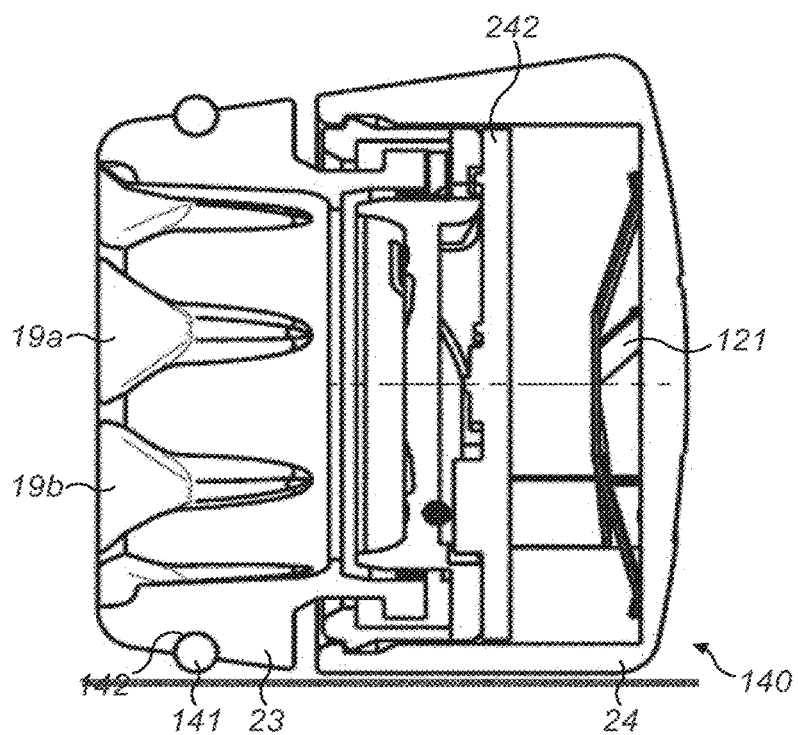
FIG. 10d is a side cross-section view of the fourth variation of the data collection device of FIG. 2.

FIG. 10b shows the slotted disc 249 that allows rotation of the first portion 23 relative to the second portion 24 to be detected and measured. The slotted disc 249 is of the corrugated type in this example. Here, the slots do not extend all the way through the disc 249 but form pits or grooves. The bottoms of the pits or grooves may be differently reflective to the surface of the disc that is closest to the sensor. Thus, movement of the disc 249 can be detected in substantially the same was as described above with reference to FIG. 7e. Further alternatively, instead of having a slotted disc, the surface of first portion 23 that is opposite to sensor 51 may be designed to be differently reflective in an alternating pattern.

The FIG. 10 data collection device is absent of a display, although a display for displaying a delivered dose may instead be provided.

Figure 11:
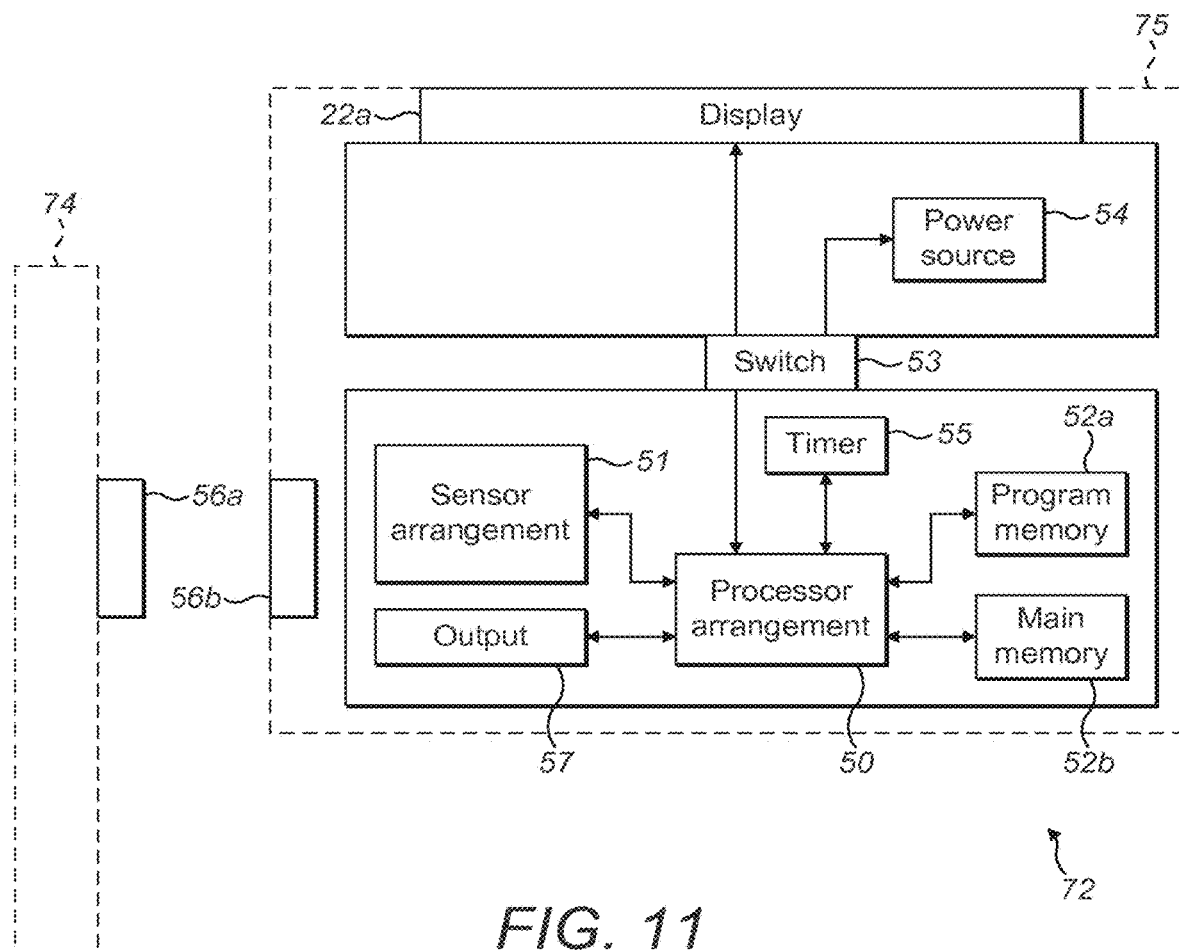
FIG. 11 is a block diagram of components of the data collection devices of FIGS. 2 and 6-10.

FIG. 11 is a block diagram of the data collection device 20, 120, 140, 220, 240. The data collection device 20 includes a processor arrangement 50 including one or more processors, such as a microprocessor, a Digital Signal Processor (DSP), Application Specific Integrated Circuit (ASIC), Field Programmable Gate Array (FPGA) or the like, together with memory units 52a, 52b, including program memory 52a and main memory 52b, which can store software for execution by the processor arrangement 50 and data generated during use of the data collection device such as counted pulses, derived dose size, time stamp, etc. The switch 53 connects the power source 54 to the electronic components of the device, including the sensor arrangement 51, when operated. The display 22a may or may not be present.

The first and second electrical contacts 30, 31 may provide a data connection between the processor arrangement 50 and display 22a when engaged.

A sensor arrangement 51, comprising one or more sensors, is provided for detecting rotational movement between the first portion 23 and the second portion 24.

The resolution of the sensing arrangement 51 is determined by the design of the injection device 1. A suitable angular resolution of the sensing arrangement 51 may be determined by Equation (1):

$$\text{resolution} = \frac{360°}{\text{units\_per\_rotation}} \qquad (1)$$

For instance, if one full rotation of the dosage knob 12 corresponds to a medicament dosage amount of 24 IU, then a suitable resolution for the sensing arrangement 51 would be not more than 15°.

In the FIG. 2 embodiment, one or more first magnets 56a are provided around a circumference of the inner surface of the first portion 23 and one or more second magnets 56b are provided around a circumference of the outer surface of the second portion 24, as shown in FIGS. 3 and 11. The sensor arrangement 51 is a transducer that varies its output due to variations in the magnetic field, based on the Hall effect, as the first portion 23 and first magnets 56a rotate relative to the second portion 24 and second magnets 56b.

Since the first portion 23 rotates with the dosage knob 12 as medicament is expelled from the injection device 1, the angle of rotation measured by the sensing arrangement 51 is proportional to the amount of medicament expelled. It is not necessary to determine a zero level or an absolute amount of medicament contained in the injection device 1. Moreover, since it is not necessary to monitor the numbers or tick marks on the number sleeve 70 displayed through the dosage window 13, the data collection device 20 may be designed so that it does not obscure the dosage window 13.

The medicament amount delivered is determined by the data collection device 20 independent from the dosage that is programmed into the injection device 1. Determining the delivered medicament amount provides a direct and thus more reliable information about the amount of medicament that is injected compared to data collection devices that determine the amount of medicament that is set, thus being intended to be dispensed.

However, in other embodiments, different types of sensor may be used. For example, instead of a transducer, the sensor arrangement may include a microelectromechanical (MEMS) device or other magnetic sensor for detecting changes in a magnetic field. Another example of an sensing arrangement is an optical encoder, including a light source, such as a light emitting diode (LED) and a light detector, such as an optical transducer, that monitors changes in light reflected from an inner surface of the first portion, where the inner surface first portion has one or regions of varying reflectivity around its circumference, such as tick marks or at least one shaped reflective region. Such a sensor arrangement is used in the second to fourth variations described above.

In some embodiments, the sensing arrangement 51 may be a potentiometer. In yet another embodiment, a capacitive sensing arrangement may be used, where elements provided on the first portion 23 affect the capacitance between two plates in the sensing arrangement. In further examples, mechanical sensors, with mechanical switches and/or tracks, may be used to detect the relative rotation between the first and second portions 23, 25.

While the embodiments described in detail includes only certain types of sensor in the sensor arrangement 51, other embodiments may be devised in which the sensor arrangement 26 includes multiple sensors of one or more types.

Figure 12:
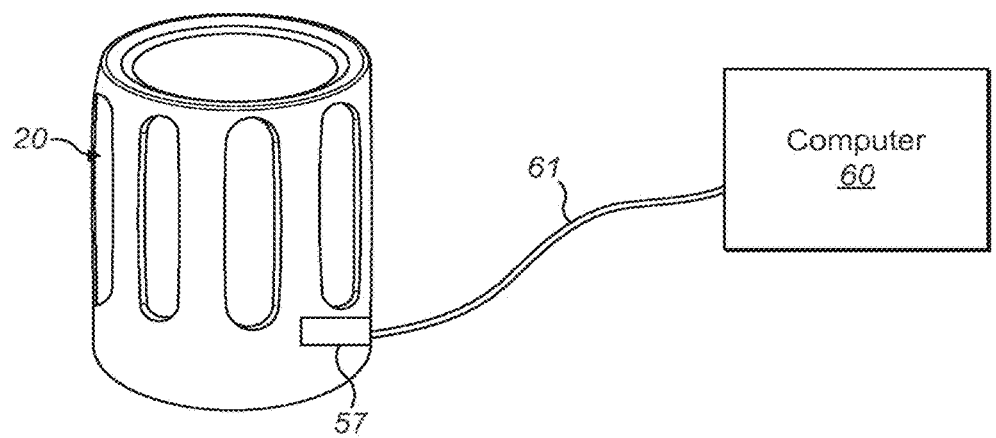
FIG. 12 depicts an example system in which data from the data collection device of FIGS. 2 and 6-10 is transmitted to another device.

An output 57 is provided, which may be a wireless communications interface for communicating with another device via a wireless network such as Wi-Fi or Bluetooth™, or an interface for a wired communications link, such as a socket for receiving a Universal Series Bus (USB), mini-USB or micro-USB connector. FIG. 12 depicts an example of a system in which the data collection device 20 is connected to another device, such as a personal computer 60, via a wired connection 61 for data transfer. For example, the processor arrangement 50 may store determined delivered medicament amounts and time stamps for the injections as they are administered by the user and subsequently, transfer that stored data to the computer 60. The computer 60 maintains a treatment log and/or forwards treatment history information to a remote location, for instance, for review by a medical professional.

According to this embodiment, the data collection device 20 is configured to store data such as delivered medicament amounts and time stamps of up to 35 injection events, According to a once-daily injection therapy this would be sufficient to store a treatment history of about one month. Data storage is organized in a first-in first-out manner ensuring that most recent injection events are always present in the memory of the data collection device 20. Once transferred to a computer 60 the injection event history in the data collection device 20 will be deleted. Alternatively, the data remains in the data collection device 20 and the oldest data is deleted automatically once new data is stored. In this way, the log in the data collection device is built up over time during usage and will always comprise the most recent injection events. Alternatively, other configuration could comprise a storage capacity of 70 (twice daily), 100 (three months) or any other suitable number of injection events depending on the therapy requirements and/or the preferences of the user.

In some embodiments, the output 57 may be configured to transmit information using a wireless communications link and/or the processor arrangement 23 may be configured to transmit such information to the computer 40 periodically.

A power switch 58 is provided, together with a power source 59. In some embodiments, the power switch 58 may be provided by the first and second electrical contacts 30, 31, or the switch 53 where the power switch 58 responds to pressure applied to the second portion 24 by powering the data collection device 20 on or off, so that power may conserved when the injection device 1 is not being used. In such an arrangement, the data collection device 20 is powered on again, the processor arrangement 50 may control the display 22a to show the determined medicament dose information 22a, to aid the memory of the user, and/or an elapsed time since the determined medicament dose was delivered. For example, the processor arrangement 23 may cause the display 22 to switch periodically between displaying the most recent determined medicament dosage information and the elapsed time.

The power source 54 may be a battery. In some embodiments, the endplate 22 may include a solar panel to recharge a rechargeable battery. The power source may be a coin cell, or multiple coin cells arranged in series or parallel.

In another embodiment, the power source 54 may be a piezo-electric generator, which generates power when the endplate 22 is pressed by the user, potentially avoiding the need for a battery.

A timer 55 is also provided. In addition to, or instead of, switching the data collection device 20 on and off, the switch 53 or the first and second electrical contacts 30, 31 may be arranged to trigger the timer 55 when engaged and/or disengaged. For example, if the timer 55 is triggered on both engagement or disengagement of the first and second electrical contacts 30, 31, or both operation and ceasing of operation of the switch 53, then the processor arrangement 50 may use the output from the timer to determine a length of time during which the injection button 11 was pressed, for example to determine the duration of an injection.

Alternatively, or additionally, the processor arrangement 50 may use the timer 55 to monitor a length of time that has elapsed since an injection was completed, as indicated by a time of disengagement of the first and second electrical contacts 30, 31 or ceasing of operation of the switch 53. Optionally, the elapsed time may be shown on the display 22*a*, as depicted in FIG. 2. Also optionally, when the first and second contacts 30, 31 are next engaged or when the switch 53 is next operated, the processor arrangement 50 may compare the elapsed time with a predetermined threshold, to determine whether a user may be attempting to administer another injection too soon after a previous injection and, if so, generate an alert such as an audible signal and/or a warning message on the display 22*a*. On the other hand, if the elapsed time is very short, it may indicate that the user is administering a medicament amount as a "split dose", and the processor arrangement 50 may store information indicating that a dosage was delivered in that manner. In such a scenario the elapsed time is compared with a predetermined threshold in the range of a few seconds, e.g. 10 seconds up to a few minutes, e.g. 5 minutes. According to an example the predetermined threshold is set to 2 minutes. If the time elapsed since the last injection is two minutes or less, the processor arrangement 50 stores information indicating that the dosage was delivered as a "split dose". Another optional purpose for monitoring the elapsed time by the processor arrangement 50 is to determine when the elapsed time has passed a predetermined threshold, suggesting that the user might have forgotten to administer another injection and, if so, generate an alert.

Figure 13:
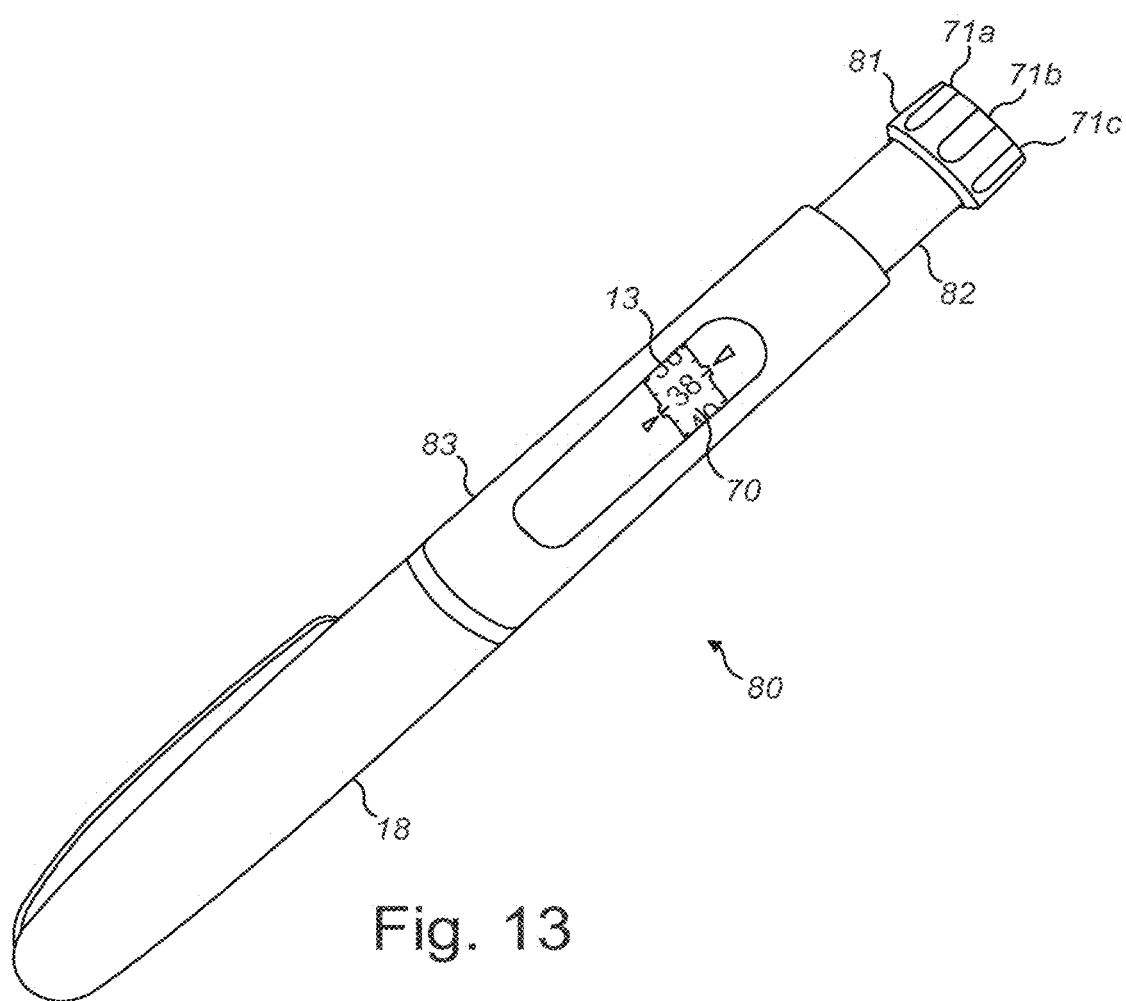
FIG. 13 is a view of an example injection device for use with a data collection device according to an embodiment of the disclosure.

The data collection device 20 is used where the injection device 1 includes a component that can rotate as medicament is dispensed. However, in some injection devices, the dosage knob does not rotate during dose delivery. However, there may be another rotatable component close to the dose knob to which the first portion 23 can be attached directly or indirectly. FIG. 13 depicts an example of such an injection device 80. In FIG. 13, components similar to those of the injection device 1 shown in FIG. 1 are indicated using the same reference labels. Also, the injection device 80 is shown with its cap 18 in place, covering the needle and medicament chamber.

In this particular example of an injection device 80, the injection button and dosage knob are provided by a single component, knob 81. A medicament dosage can be programmed into the injection device 72 by turning the knob 81, which rotates a sleeve 82 which extends outwards from a housing 83 of the injection device 70 as the programmed dosage increases. As described above in relation to FIG. 1, turning the knob 81 also turns a number sleeve 70, so that a dosage amount is displayed in the dosage window 13.

When the knob 81 is pressed to administer an injection or prime shot, the knob 81 is partially decoupled from the sleeve 82, so they can rotate independently of one another. As medicament is expelled from the injection device 80, the sleeve 82 rotates and moves into the housing 83. Meanwhile, the knob 81 moves towards the housing but does not rotate.

Figure 14:
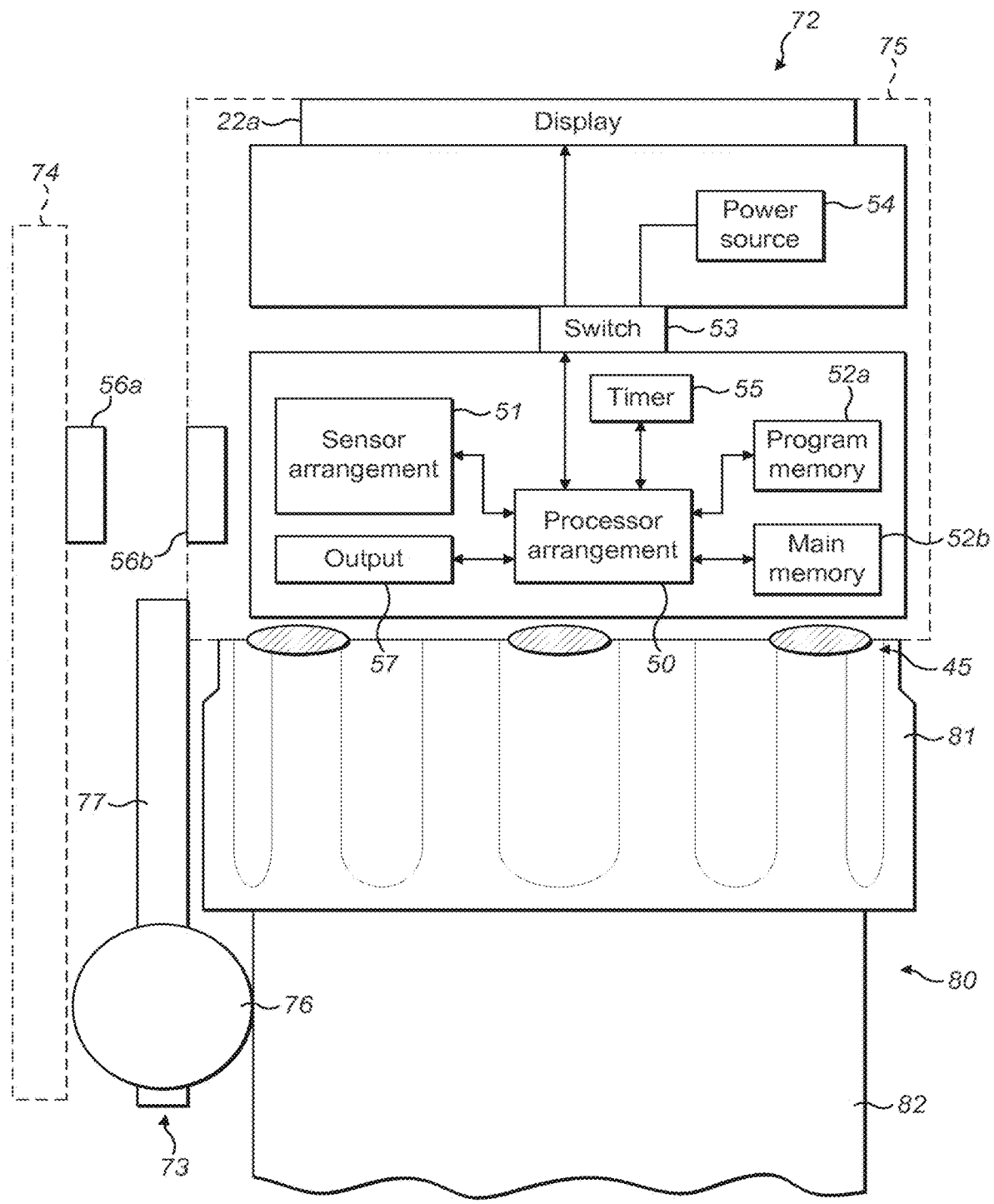
FIG. 14 is a block diagram of an example data collection device according to an embodiment of the disclosure, for use with the injection device of FIG. 13.

FIG. 14 is a block diagram of a data collection device 72 according to a further embodiment, which is capable of being used with the injection device 80 of FIG. 13 that does not have a rotatable component to which the first portion can be directly attached. Components of the data collection device 72 that correspond to those of the data collection device 20 of FIG. 2 are shown with the same reference labels.

The data collection device 72 is provided with a transfer arrangement 73. The transfer arrangement 73 is configured so that, when the data collection device 72 is attached to the injection device, it engages a component of the injection device that rotates as medicament is expelled. The transfer arrangement 73 responds to rotation of the rotatable component by causing the first portion 74 to rotate relative to the second portion 75.

In this particular example, the transfer arrangement 73 is mounted on the second portion 75 includes a friction wheel 76. In this particular example, the friction wheel 76 has a substantially spherical, or ball, shape, so that the friction wheel 76 can pass over the knob 81 when the data collection device 72 is mounted to the injection device 80 and to allow for axial movement between the first portion 74 and second portion 75, for example when using a locking mechanism similar to that described with reference to the data collection device 20 and FIG. 5. The friction wheel 76 may be attached to the second portion 75 by a resilient arm 77, to facilitate movement of the friction wheel 76 over the knob 81 when mounting or removing the data collection device 72.

While FIG. 14 depicts an embodiment in which the transfer arrangement 73 includes one friction wheel 76, other embodiments may include one or more additional friction wheels 76, such as two or three friction wheels. The provision of such additional friction wheels 76 may improve the reliability of transfer of rotation between the sleeve 82 and first portion 74.

As shown in FIG. 14, the knob 81 of the injection device 80 is in contact with the second portion 75. One or more resilient pads 45 may be provided between the second portion 75 and knob 81 to improve engagement therebetween. One or more of formations, not shown, configured to co-operate with formations 71*a*, 71*b*, 71*c* on the knob 81 of the injection device 80, resilient pads 84 and resilient portions in the second portion 75 may be provided to enhance engagement between the second portion 75 and the knob 81, so that rotation of the second portion 75 causes rotation of the knob 81 and vice versa.

However, there first portion 74 does not contact, or engage directly with, the knob 81. Therefore, the first portion 74 and second portion 75 may be locked together, as described above in relation to FIG. 5, so that the injection device 80 can be programmed by turning the first portion 74, to rotate the second portion 75 and, therefore, the knob 81. When the dosage amount has been programmed, the user may press the second portion 75, which in turn depresses the knob 81, to dispense the programmed amount of medicament from the injection device 80. The axial movement of the second portion 75 relative to the first portion 74, releases the locking mechanism that prevents rotation of the first portion 74 relative to the second portion 75.

As the medicament is expelled, the knob 81 moves towards the housing 83 but does not rotate. The sleeve 82 rotates while it moves back into the housing 83. The rotation of the sleeve 82 is transferred to the first portion 74 through the transfer arrangement 73. Therefore, the first portion 74 is caused to rotate relative to the second portion 75. The sensor arrangement 51 then detects the angle of rotation from which the medicament dosage amount can be determined, as described above in relation to the data collection device 20 of FIG. 2.

The specific embodiments described in detail above are intended merely as examples of how the present disclosure may be implemented. Many variations in the configuration of the data collection device 20, 120, 140, 240, 220 and/or the injection device 1, 80 may be used. Some such variations will now be described.

The switch 53 in the FIG. 2 embodiment is formed of electrical contacts, and in the first to fourth variations of a switch. The switch may for instance be a lever switch, a dome switch, a slider switch, a rubber keypad switch. It may be a capacitive touch switch or a resistive touch switch. It may be a tactile micro switch. The switch 53 may be generally referred to as a microswitch.

The first portion 23 may facilitate gripping by the user through radial features, as shown in FIG. 9, or a rubberized component, as shown in FIGS. 10. Alternatively, the peripheral surface of the first portion 23 may be roughened, or provided with an adhesive or tactile coating, be made of or coated with a high friction material, or have some other gripable features.

In some embodiments, a spring element is coupled to a center of the distal end of the capsule 242 at a center, proximal portion and is coupled to the first portion 23 at a distal, peripheral portion. A feature, for instance a depression, is provided on the capsule 244 to receive the center part of the spring element. When the second portion 24 is not being pressed in the distal direction, the spring element may not contact the dose button 11. When the second portion 24 is being pressed in the distal direction, the spring element compresses and communicates the force to the dose button 11. This arrangement can provide a low-friction rotation center for rotation of the first portion 23 relative to the second portion 24, along with guidance for the location of the capsule 244. It can also provide good axial tolerance compensation. Furthermore, by choosing a spring that does not compress significantly upon application of a force that is sufficient to operate the switch 53, this can provide good serial activation of the switch prior to activation of the dose delivery mechanism of the injection device 1.

Also, while the embodiments above have been described in relation to collecting data from an insulin injector pen, it is noted that embodiments of the disclosure may be used for other purposes, such as monitoring of injections of other medicaments.

The injection device 1 is configured to inject or infuse a medicament into a patient. For example, delivery could be sub-cutaneous, intra-muscular, or intravenous. Delivery could be needleless. The injection device 1 could be operated by a patient or caregiver, such as a nurse or physician, and may be one of various types of safety syringe, pen-injector, or auto-injector. The injection device 1 can include a cartridge-based system that requires piercing a sealed ampule before use. Volumes of medicament delivered with these various devices can range from about 0.5 ml to about 2 ml. The injection device 1 may be a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml). In combination with a specific medicament, the injection device 1 may also be customized in order to operate within required specifications. For example, the injection device 1 may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, the injection device 1 may include a hollow needle ranging from about 25 to about 31 Gauge in size. Common sizes are 27 and 29 Gauge.

The injection device 1 can also include one or more automated functions. For example, one or more of needle insertion, medicament injection, and needle retraction can be automated. Energy for one or more automation steps can be provided by one or more energy sources.

Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of such an injection device 1 may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to allow injection of a medicament to be provided. The injection device 1 may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. The injection device 1 may also require a specific sequence of steps to cause the one or more automated functions to occur. The injection device 1 may operate with a sequence of independent steps.

The injection device 1 can include one or more functions of a safety syringe, pen-injector, or auto-injector. For example, the injection device 1 may include a mechanical energy source configured to automatically inject a medicament (as typically found in an auto-injector) and a dose setting mechanism (as typically found in a pen-injector).

The injection device 1 may be disposable or it may be reusable.

The injection device 1 may provide a fixed dose or a user-settable dose.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin;

Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin; B29-N-(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immuno-pharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

The invention claimed is:

1. An apparatus comprising:
a data collection device which is attachable to a proximal end of an injection device, the injection device having:
a housing,
a dosage knob moveable rotationally relative to the housing for allowing a dosage of medicament to be set by a user, and
a dose delivery button moveable axially relative to the housing for allowing the user to cause delivery of medicament from the injection device,
wherein the data collection device:
includes a cavity that is configured to receive the proximal end of the injection device,
includes features that are configured to mate with one or more external features of the dosage knob of the injection device,
is configured such that, when installed on the injection device, the data collection device is not engaged with the housing of the injection device,
is configured such that, when installed on the injection device and, manipulated by the user, the data collection device affects operation of the injection device,
is configured such that, when the data collection device is rotated by the user during setting of a dosage of medicament, the dosage knob also rotates,
is configured such that movement of the data collection device in a distal direction is communicated to movement of the dose delivery button of the injection device in the distal direction,
includes a sensor arrangement which is configured to detect rotation of the dosage knob relative to the dose delivery button when a dose is being delivered, and
includes a processor arrangement that is configured to, based on the detected rotation of the dosage knob relative to the dose delivery button when the dose is being delivered, determine an amount of medicament amount expelled by the injection device.

2. The apparatus as claimed in claim 1, wherein the data collection device is configured to fit closely around the dose delivery button of the injection device.

3. The apparatus as claimed in claim 1, wherein the data collection device has formations that cooperate with formations on the dosage knob of the injection device.

4. The apparatus as claimed in claim 3, wherein, when the data collection device is placed over the dosage knob of the injection device, the formations on the dosage knob fall between the formations of the data collection device.

5. The apparatus as claimed in claim 1, wherein the injection device is configured such that, once the dose delivery button has moved enough to permit dose delivery, the dosage knob rotates relative to the dose delivery button as the dose delivery button is moved in the distal direction by action of the user.

6. The apparatus as claimed in claim 1, wherein the data collection device includes a power source.

7. The apparatus as claimed in claim 6, wherein the power source is a battery.

8. The apparatus as claimed in claim 6, wherein the power source is a coin cell.

9. The apparatus as claimed in claim 1, wherein the data collection device contains a printed circuit board.

10. The apparatus as claimed in claim 9, wherein during dialing, electronic components on the printed circuit board are not powered.

11. The apparatus as claimed in claim 1, wherein the data collection device includes a switch that is configured to be operated upon movement of the data collection device in the distal direction.

12. The apparatus as claimed in claim 11, wherein the data collection device is configured to use operation of the switch to trigger powering of components of the data collection device.

13. The apparatus as claimed in claim 1, wherein the data collection device is configured to transmit information using a wireless communications link.

14. An apparatus, comprising:
a medicament administration apparatus comprising:
an injection device having:
a housing,
a proximal end,
a dosage knob for allowing a dosage of medicament to be set by a user, and a dose delivery button for allowing the user to cause delivery of medicament from the injection device; and a data collection device, wherein the data collection device is attachable to the proximal end of the injection device, wherein the data collection device:

includes a cavity that is configured to receive the proximal end of the injection device, includes features that are configured to mate with one or more external features of the dosage knob of the injection device, is configured such that, when installed on the injection device, the data collection device is not engaged with the housing of the injection device, is configured such that, when installed on the injection device and , manipulated by the user, the data collection device affects operation of the injection device, is configured such that, when the data collection device is rotated by the user during setting of a dosage of medicament, the dosage knob also rotates, is configured such that movement of the data collection device in a distal direction is communicated to movement of the dose delivery button of the injection device in the distal direction, includes a sensor arrangement which is configured to detect rotation of the dosage knob relative to the dose delivery button when a dose is being delivered, and includes a processor arrangement that is configured to, based on the detected rotation of the dosage knob relative to the dose delivery button when the dose is being delivered, determine an amount of medicament amount expelled by the injection device.

15. The apparatus as claimed in claim 14, wherein the data collection device is configured to fit closely around the dose delivery button of the injection device.

16. The apparatus as claimed in claim 14, wherein the data collection device has formations that cooperate with formations on the dosage knob of the injection device.

17. The apparatus as claimed in claim 16, wherein, when the data collection device is placed over the dosage knob of the injection device, the formations on the dosage knob fall between the formations of the data collection device.

18. The apparatus as claimed in claim 14, wherein the injection device is configured such that, once the dose delivery button has moved enough to permit dose delivery, the dosage knob rotates relative to the dose delivery button as the dose delivery button is moved in the distal direction by action of the user.

19. The apparatus as claimed in claim 14, wherein the data collection device includes a switch that is configured to be operated upon movement of the data collection device in the distal direction.

20. The apparatus as claimed in claim 19, wherein the data collection device is configured to use operation of the switch to trigger powering of components of the data collection device.

* * * * *

UNITED STATES PATENT AND TRADEMARK OFFICE
CERTIFICATE OF CORRECTION

| | | |
|---|---|---|
| PATENT NO. | : 11,439,762 B2 | Page 1 of 1 |
| APPLICATION NO. | : 16/742219 | |
| DATED | : September 13, 2022 | |
| INVENTOR(S) | : Maurice Toporek et al. | |

It is certified that error appears in the above-identified patent and that said Letters Patent is hereby corrected as shown below:

In the Claims

Column 28, Line 5, Claim 1, delete "and," and insert -- and --

Column 29, Line 15 (approx.), Claim 14, delete "and ," and insert -- and --

Signed and Sealed this
First Day of November, 2022

Katherine Kelly Vidal
*Director of the United States Patent and Trademark Office*